(12) United States Patent
Connors et al.

(10) Patent No.: US 10,682,492 B2
(45) Date of Patent: Jun. 16, 2020

(54) EXPANDABLE BALLOON SHEATH

(71) Applicant: Medtronic Vascular, Inc., Santa Rosa, CA (US)

(72) Inventors: Alan Connors, Minneapolis, MN (US); Shyam Nagasrinivasa, Santa Rosa, CA (US); Emily Schoenhoff, Santa Rosa, CA (US); Janet Komatsu, San Francisco, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 122 days.

(21) Appl. No.: 15/875,356

(22) Filed: Jan. 19, 2018

(65) Prior Publication Data

US 2019/0224448 A1 Jul. 25, 2019

(51) Int. Cl.
*A61M 29/00* (2006.01)
*A61M 25/00* (2006.01)
*A61M 25/06* (2006.01)
*A61M 25/10* (2013.01)

(52) U.S. Cl.
CPC .... *A61M 25/0026* (2013.01); *A61M 25/0662* (2013.01); *A61M 25/10* (2013.01); *A61M 25/1025* (2013.01); *A61M 25/0074* (2013.01); *A61M 25/0668* (2013.01); *A61M 2025/0024* (2013.01); *A61M 2025/0046* (2013.01);
(Continued)

(58) Field of Classification Search
CPC .. A61M 2025/0024; A61M 2025/1081; A61M 25/0026; A61M 25/0074; A61M 25/0662; A61M 25/1025; A61M 2025/0046; A61M 2025/105; A61M 25/0668; A61M 25/10
See application file for complete search history.

(56) References Cited

U.S. PATENT DOCUMENTS

| 5,188,605 A | 2/1993 | Sleep |
| 5,383,928 A | 1/1995 | Scott et al. |
| 5,647,857 A | 7/1997 | Anderson et al. |

(Continued)

OTHER PUBLICATIONS

U.S. Appl. No. 15/875,343, filed by John Wilson Traxler et al., filed Jan. 19, 2018.

(Continued)

*Primary Examiner* — Rebecca E Eisenberg
(74) *Attorney, Agent, or Firm* — Shumaker & Sieffert, P.A.

(57) ABSTRACT

A medical device that is configured to house an expandable balloon includes a tubular sheath and a retaining member. The tubular sheath includes a longitudinal slit that extends parallel to a longitudinal axis of the tubular sheath and the retaining member is configured to retain the tubular sheath in a closed configuration. The tubular sheath may house the expandable balloon while the expandable balloon is attached to a catheter that is configured to navigate the expandable balloon into a body of a patient. The tubular sheath may be configured to house the expandable balloon substantially through the process of inserting the expandable balloon into the vasculature of the patient. Once the expandable balloon has been introduced into the introducer sheath and/or inserted into the vasculature of the patient, the retaining member may be disengaged and the tubular sheath removed from the catheter.

26 Claims, 14 Drawing Sheets

(52) U.S. Cl.
CPC .............. *A61M 2025/105* (2013.01); *A61M 2025/1081* (2013.01)

(56) References Cited

U.S. PATENT DOCUMENTS

| | | | |
|---|---|---|---|
| 5,752,937 | A | 5/1998 | Otten et al. |
| 5,868,719 | A | 2/1999 | Tsukernik |
| 5,964,730 | A | 10/1999 | Williams et al. |
| 6,110,146 | A | 8/2000 | Berthiaume et al. |
| 6,592,548 | B2 | 7/2003 | Jayaraman |
| 7,105,013 | B2 | 9/2006 | Durcan |
| 8,414,528 | B2 | 4/2013 | Liu et al. |
| 8,852,257 | B2 | 10/2014 | Liu et al. |
| 9,072,590 | B2 | 7/2015 | Wang et al. |
| 9,119,741 | B2 | 9/2015 | Liu et al. |
| 2004/0093005 | A1* | 5/2004 | Durcan ............ A61M 25/00 606/194 |
| 2006/0015171 | A1* | 1/2006 | Armstrong ...... A61B 17/12022 623/1.12 |
| 2006/0058866 | A1 | 3/2006 | Cully et al. |
| 2009/0105686 | A1 | 4/2009 | Snow et al. |
| 2010/0069852 | A1 | 3/2010 | Kelley |
| 2011/0184509 | A1* | 7/2011 | Von Oepen ............ A61F 2/95 623/1.23 |
| 2011/0208284 | A1* | 8/2011 | Hofmann ............ A61F 2/95 623/1.11 |
| 2011/0270226 | A1 | 11/2011 | Kocur et al. |
| 2012/0296313 | A1 | 11/2012 | Andreacchi et al. |
| 2013/0018309 | A1 | 1/2013 | Ewing et al. |
| 2014/0343593 | A1 | 11/2014 | Chin et al. |
| 2014/0379065 | A1 | 12/2014 | Johnson et al. |
| 2015/0088241 | A1 | 3/2015 | Liu et al. |
| 2015/0190618 | A1 | 7/2015 | Kantor |
| 2015/0328028 | A1 | 11/2015 | Wang et al. |
| 2016/0058983 | A1 | 3/2016 | Poker et al. |
| 2018/0043138 | A1 | 2/2018 | Chu |

OTHER PUBLICATIONS

U.S. Appl. No. 15/875,372, filed by John Kantor et al., filed Jan. 19, 2018.

U.S. Appl. No. 15/875,318, filed Jan. 19, 2018, naming inventors Massimo et al.

U.S. Appl. No. 15/875,331, filed Jan. 19, 2018, naming inventor Chiara Pedroni.

Office Action from U.S. Appl. No. 15/875,343, dated Nov. 15, 2019, 9 pp.

Notice of Allowance from U.S. Appl. No. 15/875,343, dated Jan. 19, 2018, 8 pp.

\* cited by examiner

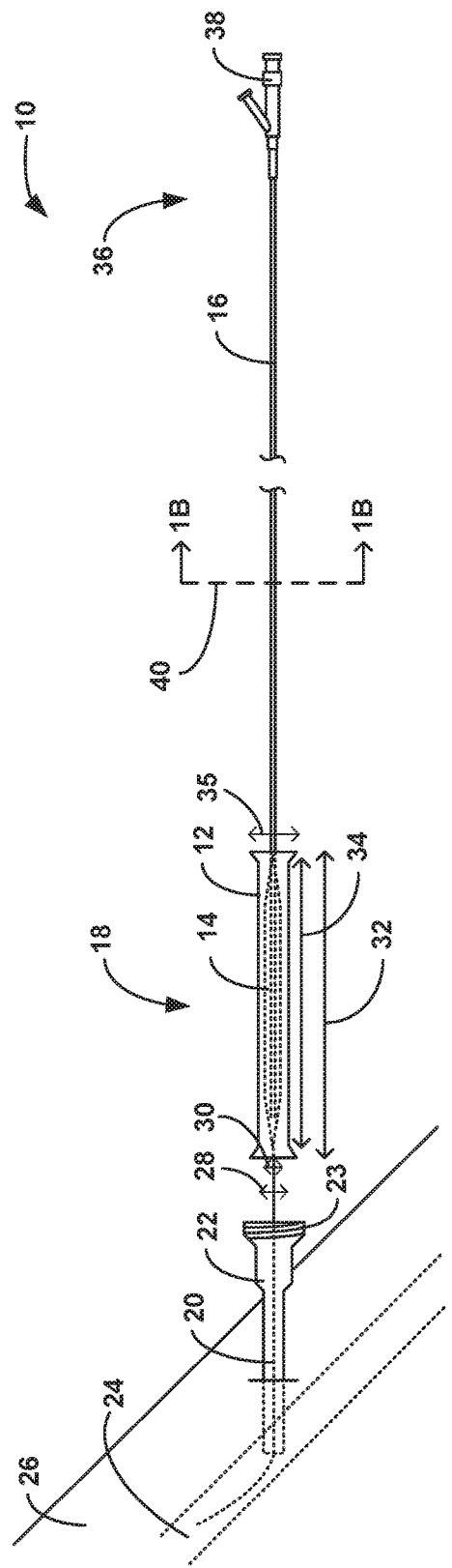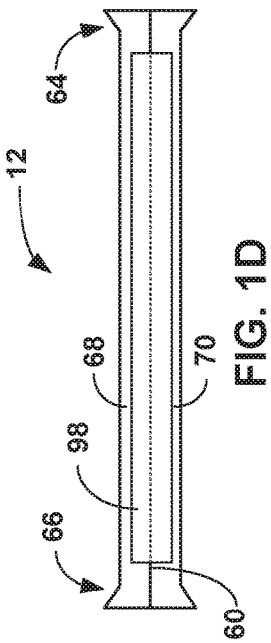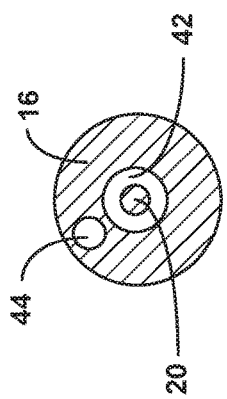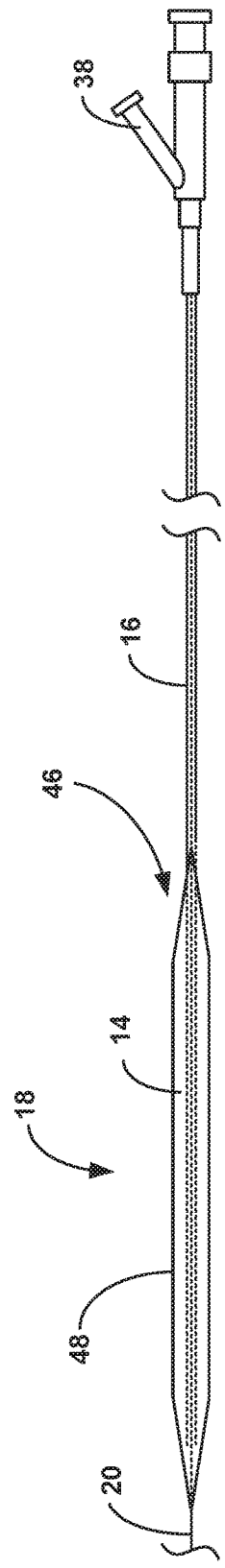

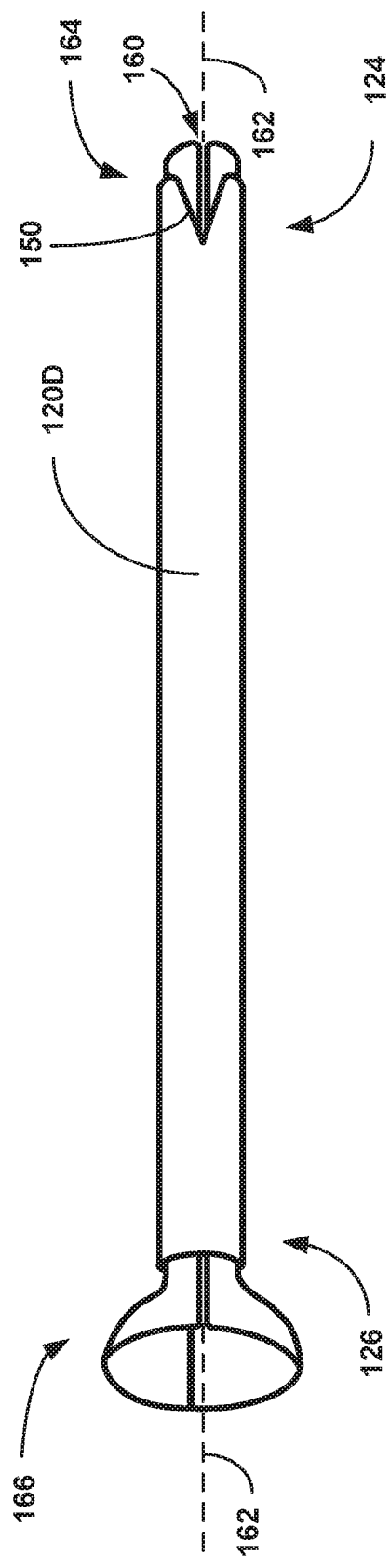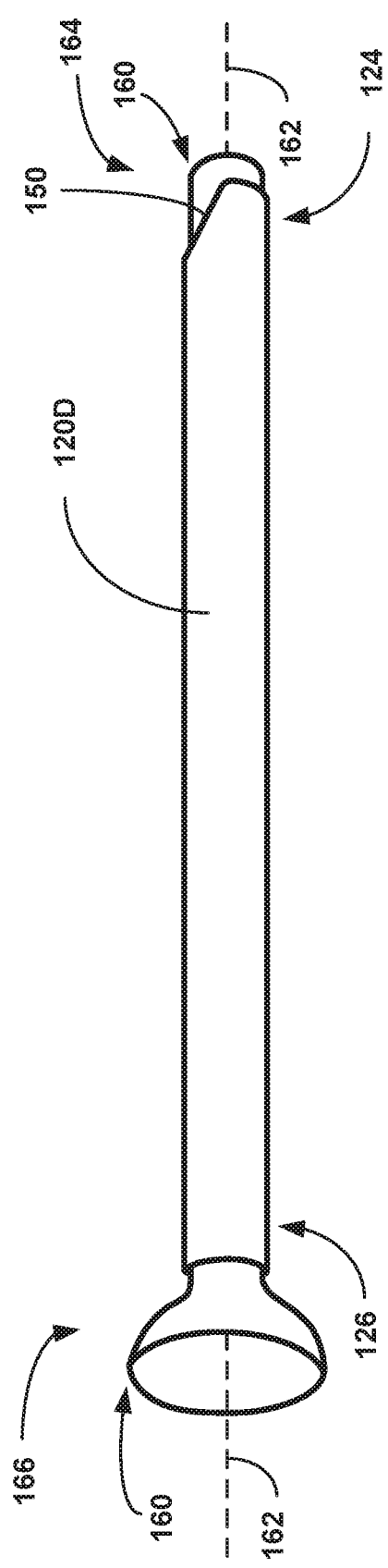

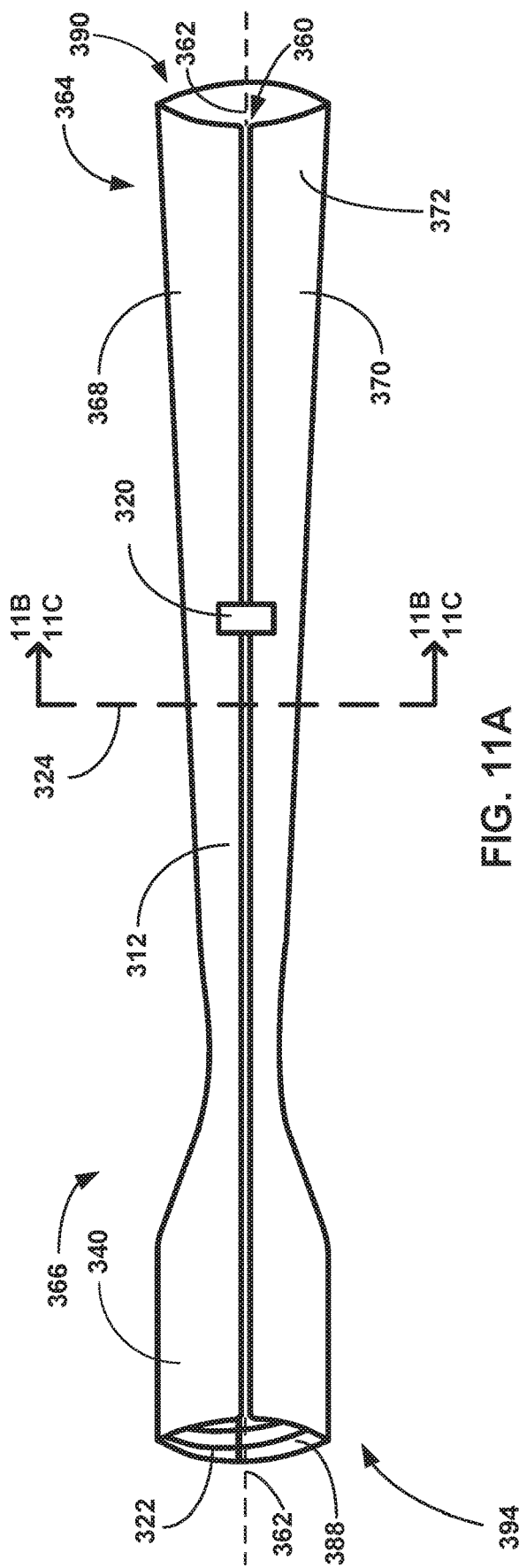
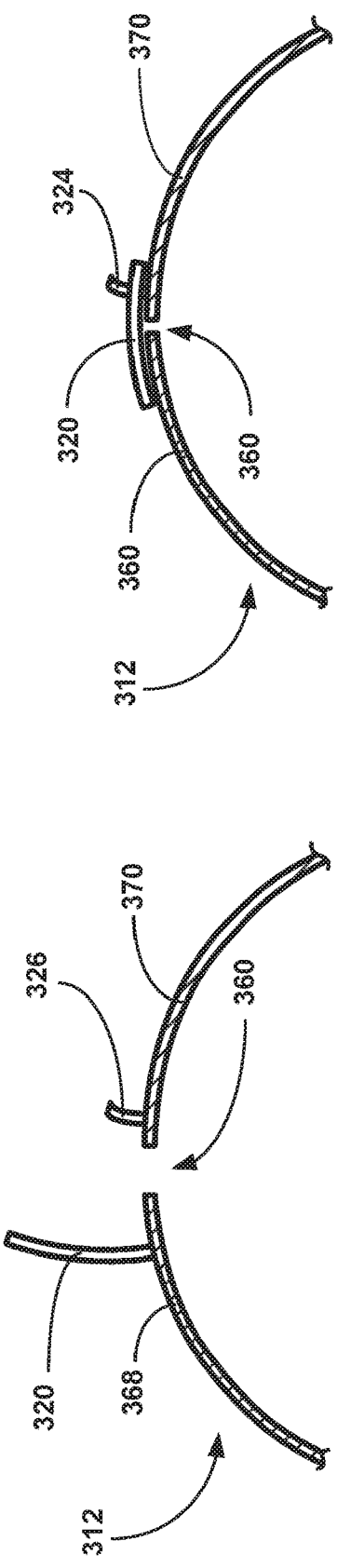
FIG. 11A
FIG. 11B
FIG. 11C

EXPANDABLE BALLOON SHEATH

TECHNICAL FIELD

This disclosure relates to medical sheaths, and more specifically expandable balloon sheaths.

BACKGROUND

Some medical treatments include the use of inflatable balloons. The expandable balloon may be inserted in a patient, such as within the vasculature of a patient, and navigated to a target site to be treated within the patient. Some expandable balloons may be fragile, such that it is easy for expandable balloons to incur damage during the insertion process. Further, some expandable balloons include coatings, such as drug coatings, which may be damaged or lost during insertion and/or navigation to the target site.

SUMMARY

In some aspects, the disclosure describes a medical device that includes a tubular sheath and a retaining member. The tubular sheath may include a longitudinal slit parallel to a longitudinal axis of the tubular sheath. The retaining member may be configured to retain the tubular sheath in a closed configuration. The medical device may be used to house an expandable balloon during packaging, storing, and inserting of the expandable balloon into a body of a patient. The expandable balloon may be attached to a catheter adjacent to the distal portion of the catheter. The catheter may be used to navigate the expandable balloon to a target site within the vasculature of a body of a patient. The tubular sheath may be configured to house the expandable balloon up to and substantially through the process of inserting the expandable balloon into the vasculature of the patient (e.g., through an introducer sheath). Once the expandable balloon has been introduced into the introducer sheath or inserted into the vasculature of the patient, the retaining member may be disengaged from the tubular sheath and the tubular sheath removed from the catheter.

In a first example, aspects of the disclosure relate to a medical device that includes a tubular sheath having an outer wall and an inner wall that defines an inner lumen configured to house an expandable balloon that is attached to a distal portion of a catheter, wherein the tubular sheath includes a longitudinal slit through the tubular sheath, wherein the longitudinal slit extends substantially parallel to a longitudinal axis of the tubular sheath and defines a first side and a second side of the longitudinal slit, wherein the longitudinal slit exposes the inner lumen. The medical device also includes a retaining member that is configured to engage the tubular sheath on both sides of the longitudinal slit to retain the tubular sheath in a closed configuration around the expandable balloon.

In a second example relating to the medical device of the first example, the retaining member is configured to disengage one or both sides of the longitudinal slit to thereby convert the tubular sheath into an open configuration such that the inner lumen is exposed and the tubular sheath can be removed from around the expandable balloon or the catheter.

In a third example relating to the medical device of the first and second example, the retaining member includes a protective sleeve that substantially covers an outer surface of the tubular sheath.

In a fourth example relating to the medical device of the third example, the protective sleeve includes a plurality of longitudinal perforations extending through a wall of the protective sleeve in a direction substantially parallel to the longitudinal axis of the tubular sheath.

In a fifth example relating to the medical device of the third example, the protective sleeve is configured to be peelable along the longitudinal axis of the tubular sheath.

In a sixth example relating to the medical device of the third example, the protective sleeve includes a film that has been heat shrunk onto the outer surface of the tubular sheath.

In a seventh example relating to the medical device of any of the third through sixth examples, the protective sleeve includes a tab attached to an end of the protective sleeve, wherein the protective sleeve is configured to be removed from the tubular sheath in a controlled manner in response to a force above a threshold force being exerted upon the tab.

In an eighth example relating to the medical device of any of the first through seventh examples, the retaining member defines a notched groove that extends longitudinally along the longitudinal axis of the tubular sheath, wherein the notched groove aligns with the longitudinal slit of the tubular sheath.

In a ninth example relating to the medical device of the first example, the retaining member includes a strip of adhesive that substantially covers the longitudinal slit to adhere the sides of the tubular sheath on each side of the longitudinal slit to each other, wherein the strip of adhesive is configured to be removeable along the longitudinal axis of the tubular sheath.

In a tenth example relating to the medical device of the first example, the retaining member includes a suture that is configured to stitch together the tubular sheath across the longitudinal slit.

In an eleventh example relating to the medical device of the tenth example, the suture includes a tab attached to an end of the suture, wherein the suture is configured to unravel in a controlled manner in response to a force above a threshold force being exerted upon the tab.

In a twelfth example relating to the medical device of the first example, the retaining member includes at least one ring that is configured to extend around a circumference of the tubular sheath, wherein the at least one ring is slideable along the longitudinal axis of the tubular sheath to remove the at least one ring from the tubular sheath.

In a thirteenth example relating to the medical device of the first example, the retaining member includes a clasp on the tubular sheath on one side of the longitudinal slit and a mating element on the tubular sheath on the other side of the longitudinal slit, wherein the clasp is configured to engage the mating element to retain the tubular sheath in the closed configuration.

In a fourteenth example relating to the medical device of any of the first through thirteenth examples, the tubular sheath is configured to be slideable over the catheter, wherein the tubular sheath is configured to engage and distally displace a storage sheath that is covering the expandable balloon when the expandable balloon is on the distal portion of the catheter without substantial contact to the expandable balloon when the tubular sheath is on the catheter proximal to the protective sleeve.

In a fifteenth example relating to the medical device of any of the first through fourteenth examples, a distal portion of the tubular sheath is flared outward from the longitudinal axis of the tubular sheath.

In a sixteenth example relating to the medical device of any of the first through fifteenth examples, a proximal portion of the tubular sheath is flared outward from the longitudinal axis of the tubular sheath.

In a seventeenth example relating to the medical device of any of the first through sixteenth examples, the inner wall that defines the lumen of the tubular sheath is coated with a lubricious material to reduce friction between the tubular sheath and the expendable balloon.

In an eighteenth example relating to the medical device of any of the first through seventeenth examples, the medical device includes a Luer fitting on a distal end of the tubular sheath, wherein the Luer fitting includes a structural weakness aligned with the longitudinal slit to enable the Luer fitting to be controllably split along the structural weakness.

In a nineteenth example relating to the medical device of any of the first through eighteenth examples, the expandable balloon is coated with a drug coating.

In a twentieth example relating to the medical device of any of the first through nineteenth examples, a thickness between the inner and outer walls of the tubular sheath is substantially constant throughout the tubular sheath.

In a twenty-first example relating to the medical device of any of the first through twentieth examples, the tubular sheath includes at least one of poly(tetrafluoroethylene), high density polyethylene, and low density polyethylene.

In a twenty-second example relating to the medical device of any of the first through twenty-first examples, the balloon is in a deflated state on the distal portion of the catheter, and a diameter of the inner lumen is configured to be greater than an outer diameter of the expandable balloon in the deflated state.

In a twenty-third example relating to the medical device of the twenty-second example, a length of the tubular sheath along the longitudinal axis of the tubular sheath is configured to be greater than a length of the expandable balloon along a longitudinal axis of the expandable balloon in the deflated state.

In a twenty-fourth example, aspects of the disclosure relate to a method of inserting expandable balloons that includes positioning a distal portion of a catheter of a medical device immediately proximal to an introducer sheath implanted in a body of a patient. The medical device includes a tubular sheath having an outer wall and an inner wall that defines an inner lumen configured to house an expandable balloon that is attached to the distal portion of the catheter, wherein the tubular sheath includes a longitudinal slit through the tubular sheath, wherein the longitudinal slit extends substantially parallel to a longitudinal axis of the tubular sheath and defines a first side and a second side of the longitudinal slit, wherein the longitudinal slit exposes the inner lumen. The medical device also includes a retaining member that is configured to engage the tubular sheath on both sides of the longitudinal slit to retain the tubular sheath in a closed configuration around the expandable balloon. The method of inserting expandable balloons also includes disengaging the retaining member from the tubular sheath to thereby convert the tubular sheath into an open configuration subsequent to inserting the expandable balloon into the introducer sheath. The method of inserting expandable balloons also includes removing the tubular sheath from the catheter in response to inserting the expandable balloon into the introducer sheath and converting the tubular sheath into an open configuration subsequent to disengaging the retaining member.

In a twenty-fourth example, aspects of the disclosure relate to a method of inserting expandable balloons that includes positioning an inner lumen defined by an inner wall of a tubular sheath over a catheter that is configured to navigate vasculature of a patient, an expandable balloon attached to a distal portion of the catheter and a storage sheath covering the expandable balloon on the distal portion of the catheter, wherein the tubular sheath is positioned proximal to the storage sheath. The tubular sheath includes an outer wall and the inner wall, a longitudinal slit through the tubular sheath that extends substantially parallel to a longitudinal axis of the tubular sheath and defines a first side and a second side of the longitudinal slit, wherein the longitudinal slit exposes the inner lumen, and a retaining member that is configured to engage the tubular sheath on both sides of the longitudinal slit to retain the tubular sheath in a closed configuration around the expandable balloon. The method of inserting expandable balloons also includes engaging the retaining member across both sides of the longitudinal slit to retain the tubular sheath in a closed configuration with the catheter within the inner lumen of the tubular sheath. The method of inserting expandable balloons also includes engaging the retaining member across both sides of the longitudinal slit to retain the tubular sheath in a closed configuration with the catheter within the inner lumen of the tubular sheath distally pushing the tubular sheath until the tubular sheath engages and distally pushes the storage sheath off the catheter without substantial contact to the expandable balloon. The method of inserting expandable balloons also includes locating the distal portion of the catheter immediately proximal to an introducer sheath implanted in the body of a patient and pushing the expandable balloon through the tubular sheath into the introducer sheath. The method of inserting expandable balloons also includes disengaging the retaining member from at least side of the tubular sheath across the longitudinal slit to thereby convert the tubular sheath into an open configuration in response to inserting the expandable balloon into the introducer sheath and removing the tubular sheath from the catheter in response to converting the tubular sheath into the open configuration.

In a twenty-fifth example, aspects of the disclosure relate to a medical device that includes a catheter that is configured to navigate vasculature of a body of a patient and an expandable balloon arranged in a deflated state on a distal portion of the catheter. The medical device also includes a tubular sheath having an outer wall and an inner wall that defines an inner lumen that is configured to house the expandable balloon in the deflated state on the distal portion of the catheter, where a diameter of the inner lumen is configured to be greater than an outer diameter of the expandable balloon in the deflated state and a length of the tubular sheath along a longitudinal axis of the tubular sheath is configured to be greater than a length of the expandable balloon along a longitudinal axis of the expandable balloon in the deflated state. The tubular sheath includes a longitudinal slit through the tubular sheath that extends substantially parallel to a longitudinal axis of the tubular sheath and defines a first side and a second side of the longitudinal slit. The longitudinal slit exposes the inner lumen. The medical device also includes a retaining member that is configured to engage the tubular sheath on both sides of the longitudinal slit to retain the tubular sheath in a closed configuration around the expandable balloon.

The details of one or more examples are set forth in the accompanying drawings and the description below. Other features, objects, and advantages will be apparent from the description and drawings, and from the claims.

BRIEF DESCRIPTION OF THE DRAWINGS

FIG. 1A is a conceptual and schematic diagram illustrating a view of an example medical device including an example tubular sheath housing an example expandable balloon on an example catheter near an example introducer sheath inserted in a body of a patient.

FIGS. 1B-1D are views of the medical device of FIG. 1A, including a cross-sectional view of the catheter of FIG. 1A (FIG. 1B) and conceptual and schematic diagrams illustrating a view of the tubular sheath and retaining member (FIG. 1D) and a view of the expandable balloon on the catheter without the tubular sheath (FIG. 1C).

FIGS. 7A and 7B are conceptual and schematic diagrams illustrating side views of a tubular sheath and an example retaining member, with two side views rotated 90° relative to each other around a longitudinal axis of the tubular sheath.

FIGS. 11A-11C are conceptual and schematic diagrams illustrating a side view of an example tubular sheath with an example retaining member (FIG. 11A) and cross-sectional views of the example retaining member taken along cut plane 324 not engaging (FIG. 11B) and engaging FIG. 11C) both sides of the tubular sheath, respectively.

DETAILED DESCRIPTION

Figure 2A:
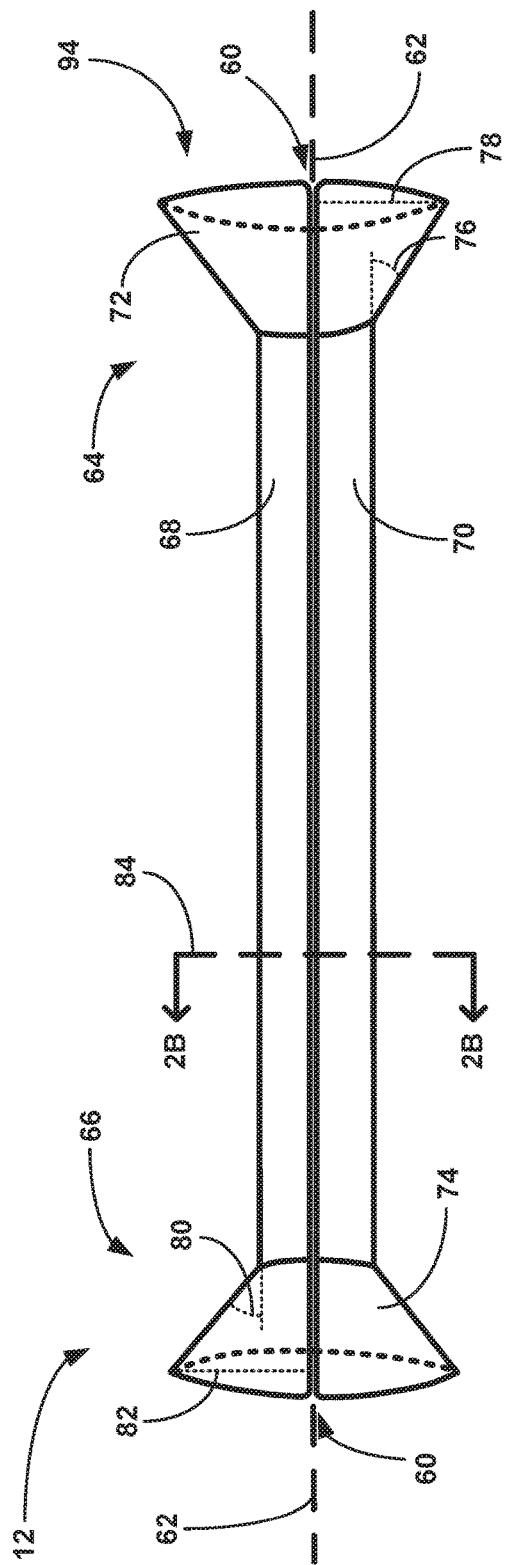
FIGS. 2A-2C are conceptual and schematic diagrams illustrating a side view of the tubular sheath of FIG. 1A in the closed configuration (FIG. 2A), cross-sectional view of the tubular sheath of FIG. 2A taken along cross-sectional plane 84 (FIG. 2B), and side view of the tubular sheath of FIG. 1A in the open configuration (FIG. 2C).

In general, the disclosure describes an example medical device that includes a tubular sheath and a retaining member. The tubular sheath may include a longitudinal slit parallel to a longitudinal axis of the tubular sheath. The retaining member may be configured to retain the tubular sheath in a closed configuration and may be removable from the tubular sheath to enable the tubular sheath to convert the tubular sheath into an open configuration. The medical device may be used to house an expandable balloon during packaging, storing, and inserting of the expandable balloon in a body of a patient.

Expandable medical balloons are used in a variety of medical procedures, such as angioplasty, tuboplasty, or pyeloplasty. In medical procedures, the expandable balloon may be attached to a catheter that is configured to navigate the expandable balloon to a target site. The target site may be a location within a patient's body where the procedure is performed. In some medical procedures, the expandable balloon may be navigated to the target site in an unexpanded (deflated) state and be expanded (inflated) at the target site as part of the medical procedure.

The expandable balloon and catheter shaft may be relatively delicate, being prone to kinking or flexing in ways that damage the structural integrity of the expandable balloon, the catheter shaft, or both. For example, if handled improperly, the expandable balloon may become stuck to itself or become stretched, such that upon being inflated later the expandable balloon may not inflate evenly or in the intended shape, or may inflate with an undesired weakness (e.g., the weakness making the expandable balloon more susceptible to bursting or breaking). Further, if handled improperly, during insertion the catheter shaft may kink or otherwise deform such that an inflation port of the catheter (e.g., a port and lumen used to inflate the expandable balloon) is damaged and becomes difficult or impossible to use to properly inflate the expandable balloon subsequent to insertion. The tubular sheaths described herein may house and protect or shield the expandable balloon until it is no longer possible/practicable to house the expandable balloon (e.g., upon inserting the expandable balloon into an introducer sheath inserted in a patient). Further, housing the expandable balloon in the tubular sheaths described herein may reduce or eliminate contact between the expandable balloon and a user such as a clinician that is manipulating the expandable balloon. This may reduce the likelihood of kinking or flexing the expandable balloon.

Further, in some expandable balloons, an external surface of the expandable balloon may be coated with a drug, which is delivered to the target site upon expanding the expandable balloon. For example, the drug may be intended to stop a hyperproliferative response of an intima within the vasculature of a patient. Such drug coatings may have relatively low adhesion to the expandable balloon such that contact between the drug coating and other surfaces or structures may remove some drug coating from the external surface of the expandable balloon. This may increase variability and/or unpredictability in an amount of drug delivered to the target site, both of which are undesirable. The tubular sheaths described herein may reduce inadvertent removal of drug from the surface of a coated expandable balloon. One advantage to the tubular sheaths described herein is that they can each be put into an open configuration and wrapped around the expandable balloon, and not necessarily have to be slid over the expandable balloon. This is advantageous because sliding a device over an expandable balloon may damage the balloon itself or any coating thereon.

FIG. 1A is a conceptual and schematic diagram illustrating a view of an example medical device 10 including a tubular sheath 12 having a retaining member 98 (FIG. 1D). The medical device 10 may additionally include an expandable balloon 14 and a catheter 16. The tubular sheath 12 may be configured to house the expandable balloon 14. The expandable balloon 14 may be attached to the catheter 16 adjacent to a distal portion 18 of the catheter 16. In some examples, the expandable balloon 14 is fixedly attached adjacent to the distal portion 18 of the catheter 16, such that it is difficult or impossible to remove the expandable balloon 14 from the catheter 16 without damaging one or both of the expandable balloon 14 or the catheter 16. In other examples, the expandable balloon 14 is loosely or removably attached to the catheter 16, such that the expandable balloon 14 may be detached from the catheter 16 once the expandable balloon 14 is navigated to the target site.

In some examples, the system in which the medical device 10 is utilized may include an introducer sheath 22. The introducer sheath 22 may be inserted in the patient transcutaneously in order to access vasculature 24 of a patient 26. In some examples, the introducer sheath 22 may include external threads 23, which may be configured to mate with complementary threads defined in the tubular sheath 12. In other examples, the introducer sheath 22 may omit the external threads 23. An internal diameter of the introducer sheath 22 may be selected to accommodate an external diameter of the expandable balloon 14 (e.g., in a deflated state) and an external diameter of the catheter 16.

The vasculature 24 of the patient 26 in which the introducer sheath 22 is inserted may be selected to provide access to a selected target site to which the expandable balloon 14 will be advanced. For example, the expandable balloon 14 may be used to provide anti-restenotic therapy to a target site in a peripheral vasculature of a patient 26.

The catheter 16 extends from a proximal portion 36 adjacent to a hub 38, such as a manifold, to the distal portion 18 that is connected to the expandable balloon 14. The catheter 16 may include structural features that enable expansion or inflation of the expandable balloon 14 and advancing of the expandable balloon 14 to the target site in the patient 26. For example, the catheter 16 may include a guidewire lumen 42 and an inflation lumen 44 (FIG. 1B).

FIG. 1B is a conceptual and schematic diagram illustrating a cross-sectional view of the catheter 16 from the cross-sectional cut plane 40 in FIG. 1A. The guidewire lumen 42 may be configured to receive a guidewire 20. In some examples, the guidewire lumen 42 may extend longitudinally through the catheter 16 from the distal portion 18 to the hub 38. The hub 38 may include a first port that provides access to the guidewire lumen 42 to facilitate advancing the catheter 16 along the guidewire 20. Similarly, the inflation lumen 44 may be configured to extend longitudinally through the catheter 16 from the hub 38 to the expandable balloon 14. The hub 38 may include a second port that provides access to the inflation lumen 44. The inflation lumen 44 may terminate distally at an orifice to the interior of the expandable balloon 14. The inflation lumen 44 may be configured to receive a fluid that is flowed into the inflation lumen 44 from the hub 38 to expand, or inflate, the expandable balloon 14 (e.g., once the expandable balloon 14 has been navigated to the target site). Though the guidewire lumen 42 and inflation lumen 44 are depicted in FIG. 1B as separate lumens with distinct axes for purposes of clarity, in other examples guidewire lumen 42 and inflation lumen 44 may be coaxial or bilumen.

FIG. 1C is a conceptual and schematic diagram illustrating a side view of the expandable balloon 14 as arranged on the catheter 16 without the tubular sheath 12. As depicted in FIG. 1C, the expandable balloon 14 is in a deflated configuration 46, which includes the expandable balloon 14 being folded into a physically smaller profile than the profile of the expandable balloon 14 in an inflated configuration. It is to be understood that the general shape of the deflated configuration 46 in FIG. 1C is for illustration purposes only; other shapes and configurations of the expandable balloon 14 in a non-inflated (or deflated) configuration 46 are also possible. Further, as depicted in FIG. 1C, the guidewire 20 extends from a position distal to the expandable balloon 14 longitudinally through the catheter 16 to the hub 38. In some examples, the guidewire 20 may be advanced through the vasculature 24 of a patient 26 during a previous step, such that the catheter 16 is advanced over the guidewire 20 using the guidewire lumen 42 to navigate the expandable balloon 14 to the target site (e.g., using the Seldinger technique). During such a technique, the guidewire 20 may only extend as far proximally through the guidewire lumen 42 as the catheter 16 has been pushed distally along the guidewire 20.

The expandable balloon 14 may be formed from any suitable material that provides sufficient strength and flexibility for the pressures experienced by the expandable balloon 14 during the inflation procedure. The materials from which the expandable balloon 14 is formed may be biocompatible and compatible with a drug coating on the external surface 48 of the expandable balloon 14. In some examples, materials from which the expandable balloon 14 is formed may include nylon, polyethylene terephthalate (PET), polyethylene (such as crosslinked polyethylene), polyurethane, polyvinyl chloride, silicone elastomer, or the like.

In some examples, the expandable balloon 14 may include a coating on an external surface 48 of the expandable balloon. The coating may include, for example, a lubricious coating (either hydrophilic or hydrophobic), a drug coating, or the like. In some examples, the drug coating may include a drug selected to treat peripheral artery disease, such as an anti-restenotic or anti-proliferative drug. An example anti-proliferative drug is paclitaxel. In some examples, the drug coating may further include an excipient to facilitate release of the drug from the drug coating. Example excipients include urea, polysorbate, sorbitol, or the like.

FIG. 1D is a conceptual and schematic diagram illustrating a side view of the tubular sheath 12. The tubular sheath 12 includes a longitudinal slit 60. The longitudinal slit 60 may extend from a proximal end 64 of the tubular sheath 12 to a distal end 66 of the tubular sheath 12. The longitudinal slit 60 may separate or bisect a first side 68 and second side 70 of the tubular sheath 12. For clarity, in some embodiments, the first side 68 and the second side 70 of the tubular sheath are portions of an otherwise continuous tube separated by the longitudinal slit 60. In other embodiments, the first side 68 and the second side 70 of the tubular sheath are portions of a tube that are joined together to form an enclosed cylindrical tube. The longitudinal slit 60 is configured to enable the removal of the tubular sheath 12 from the catheter 16 by facilitating the tubular sheath 12 being split open between the first side 68 and second side 70 of the tubular sheath 12.

A retaining member 98 is configured to retain the tubular sheath 12 closed (e.g., closed upon the catheter 16). The retaining member 98 may be configured to retain the tubular sheath in this closed configuration by engaging both the first side 68 and the second side 70 over the longitudinal slit 60. The size and shape of the retaining member 98 of FIG. 1D is for illustrative purposes only, and other shapes, sizes, and configurations of retaining members 98 as discussed and suggested herein are within the scope of this disclosure.

The tubular sheath 12 is configured to house the expandable balloon 14. For example, the tubular sheath 12 may be configured to house the expandable balloon 14 during storage, handling, and at least an initial portion of a treatment procedure. The tubular sheath 12 may be configured to support the expandable balloon 14 during the insertion of the expandable balloon 14 (e.g., insertion into the introducer sheath 22) so that the expandable balloon 14 does not bend or kink during insertion. In some examples, the tubular sheath 12 is sized relative to the expandable balloon 14 so that contact between the expandable balloon 14 and the tubular sheath 12 is reduced or minimized. For example, an internal diameter 28 of the tubular sheath 12 may be greater than an external diameter 30 of the expandable balloon 14 when the expandable balloon 14 is in the deflated configuration 46. Further, a longitudinal length 32 of the tubular sheath 12 may be configured to be greater than a longitudinal length 34 of the expandable balloon 14. For example, the tubular sheath 12 may be configured to be at least 300 millimeters long (e.g., as such a length may cover many varieties of expandable balloons 14). Configuring the tubular sheath 12 to substantially cover the expandable balloon 14 while reducing or minimizing contact between the tubular sheath 12 and the expandable balloon 14 may increase the physical integrity of both the expandable balloon 14 and any drug coating on the expandable balloon 14, as contact may result in the expandable balloon 14 kinking and/or a portion of the drug coating being partially removed.

The tubular sheath 12 may be configured to define a relatively reduced profile, such that an outer diameter 35 of the tubular sheath 12 is nearly equal to an external diameter 30 of the deflated state of the expandable balloon 14 (e.g., the tubular sheath 12 may define an external diameter 30 that is less than two times the external diameter 30 of the deflated state of the expandable balloon 14). In some examples, the outer surface of the tubular sheath 12 may define a generally continuous and tubular outer surface (e.g., an outer surface that does not define large ridges or lips that double or triple a diameter of the tubular sheath 12). Put differently, a longitudinal profile of the tubular sheath 12 may be configured to avoid extending out radially from the relative shape of the expandable balloon 14 more than what facilitates moving the tubular sheath 12 on the catheter 16 as described herein. For example, other than a proximal flare 64 and distal flare 66 as discussed below with respect to FIG. 1D, tubular sheath 12 may omit features that substantially extend radially outward (e.g., extend outward to more than two or three times an internal diameter 28 of the tubular sheath 12).

The expandable balloon 14 may be stored and shipped attached to the catheter 16 within a channel or lumen of a container, where removing the expandable balloon 14 and catheter 16 from the container may include a clinician longitudinally extracting the catheter 16 (and the expandable balloon 14) through the channel or lumen. In examples in which a clinician removes the medical device 10 from a container by longitudinally traversing the medical device 10 through a channel or lumen, the channel or lumen of a container must be at least as large as the greatest radius as the medical device 10 that the container will store. Thus, reducing the longitudinal profile of the tubular sheath 12 may reduce a size of the container used to store the medical device 10.

The tubular sheath 12 may be configured to generally maintain a stable position on the catheter 16 relative to the catheter 16 as the catheter 16 is handled. For example, the tubular sheath 12 may be configured to maintain a position over the expandable balloon 14 such that the tubular sheath 12 substantially always houses the expandable balloon 14 as the catheter 16 is handled/moved by a clinician (e.g., whether or not the clinician is specifically handling/holding the tubular sheath 12 in place) until insertion of the expandable balloon 14 into the introducer sheath 22. In some examples, the tubular sheath 12 is configured to be moved relative to the catheter 16 (e.g., subsequent to a retaining member exposing the expandable balloon 14 as described herein) in response to the clinician applying more than a threshold force upon the tubular sheath 12 and/or a retaining member as described herein, where the threshold force is more than a nominal force (e.g., gravity or incidental contact as a result of the tubular sheath 12 unintentionally or otherwise minimally contacts an object). The tubular sheath 12 may be configured to maintain a relatively stable position on the catheter 16 because of a fit of the tubular sheath 12 on the expandable balloon 14 (e.g., a friction fit). Configuring the tubular sheath 12 to generally maintain a stable position on the catheter 16 relative to the catheter 16 while a clinician is handling the medical device 10, whether or not the tubular sheath 12 is purposefully externally supported (e.g., supported by the clinician) during such handling, may improve an ability of the tubular sheath 12 to house and protect the expandable balloon 14, catheter 16, or both during handling and insertion of the expandable balloon 14 and the catheter 16 into introducer sheath 22.

The tubular sheath 12 may be configured to house the expandable balloon 14 until and/or as the expandable balloon 14 is inserted into the introducer sheath 22 (which is itself inserted in the vasculature 24 of the patient 26). As discussed above in FIG. 1D, the tubular sheath 12 includes a longitudinal slit 60 that enables tubular sheath 12 to be opened and removed from the catheter 16. The tubular sheath 12 may be configured to be removed concurrently with and/or after the expandable balloon 14 being inserted into the introducer sheath 22. Additionally, a retaining member 98 may engage the tubular sheath 12 on both sides 68, 70 of longitudinal slit to retain the tubular sheath 12 in a closed configuration that houses the expandable balloon 14. By removing or disengaging the retaining member 98 from the tubular sheath 12, the tubular sheath 12 may attain an open configuration that enables the tubular sheath 12 to be removed from the catheter 16.

The tubular sheath 12 may be configured to be removed from the expandable balloon 14 while or after the expandable balloon 14 is being inserted into the introducer sheath 22. For example, the tubular sheath 12 may be configured such that a section of the tubular sheath 12 is opened as a respective portion of expandable balloon 14 that is housed by the section of the tubular sheath 12 is immediately proximal to the introducer sheath 22. Such a configuration may result in respective portions of the expandable balloon 14 being protected/retained by the tubular sheath 12 until the respective portion of the expandable balloon 14 is or is about to be inserted into the introducer sheath 22 (e.g., while still retaining a more proximal portion of the expandable balloon 14).

Alternatively, the tubular sheath 12 may be configured to be removed after the expandable balloon 14 is fully inserted into the introducer sheath 22. To facilitate this, the tubular sheath 12 may be configured to be slidably mounted on the catheter 16. For example, the tubular sheath 12 may be configured to slide proximally relative to the catheter 16 when the catheter 16 is pushed distally into the introducer sheath 22. Alternatively, the tubular sheath 12 may be configured to slide proximally relative to the catheter 16 to be pushed over the introducer sheath 22, and may include threads that mate with external threads 23 of the introducer sheath 22. In such ways, the tubular sheath 12 is configured to protect the expandable balloon 14 until the expandable balloon 14 is inserted into the introducer sheath 22. This may reduce or substantially eliminate manual handling of the expandable balloon 14 by a user such as a clinician, which may result in structural/pharmaceutical benefits for the medical device 10. For example, manually handling the expandable balloon 14 may increase the risk of physically damaging the expandable balloon 14 or unnecessarily removing drug coating from the expandable balloon 14, such that avoiding manually handling the expandable balloon 14 is advantageous. As another example, the tubular sheath 12 may provide structural support to the expandable balloon 14 during insertion of the expandable balloon into the introducer sheath 22.

Further, configuring the tubular sheath 12 to be both removable and slideable on the catheter 16 may increase the operational length of the catheter 16 during a medical procedure. For example, if a tubular sheath 12 was slideable but not removable, in response to the tubular sheath 12 being slid proximally back to a proximal portion 36 of the catheter, a length of the catheter 16 that is equal to the length 32 of the tubular sheath 12 may be operationally unusable (e.g., as the tubular sheath 12 is neither able to slide proximally over the hub 38 of the catheter 16 nor able to be inserted into the introducer sheath 22). In some examples, it may be advantageous to delay removing the tubular sheath 12 from the catheter 16 until the expandable balloon 14 is distally past the introducer sheath 22 into the vasculature 24 of the patient 26, as the act of insertion may be complicated and prone for error (such that minimizing the steps thereof is useful in reducing the likelihood of error) in comparison to the act of vasculature 24 navigation.

Figure 2C:
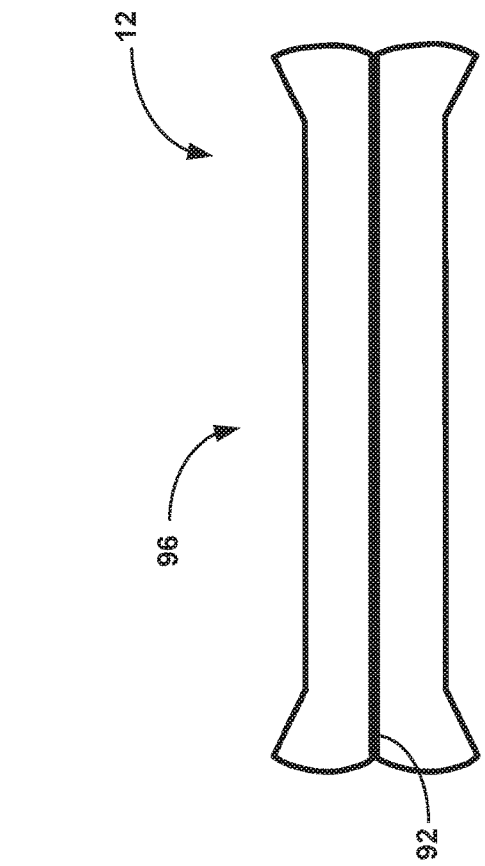
Figure 2B:
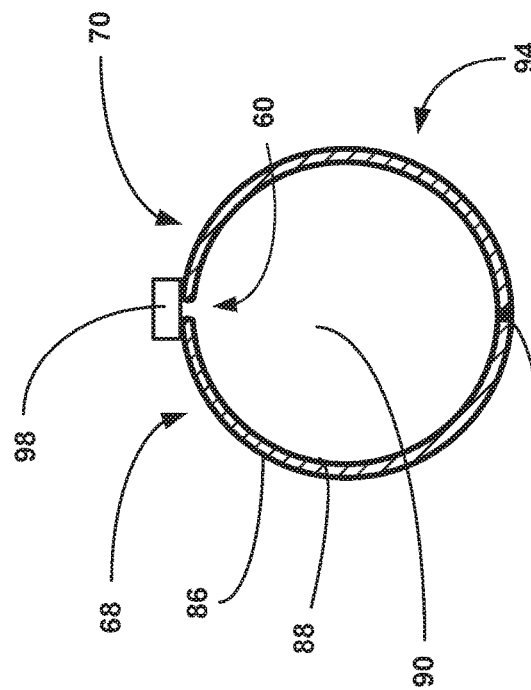

FIGS. 2A-2C are conceptual and schematic diagrams illustrating a side view (FIG. 2A), cross-sectional view (FIG. 2B), and side view (FIG. 2C) of the tubular sheath 12 of FIG. 1A, respectively. The tubular sheath 12 may be made of any suitable material, such as poly(tetrafluoroethylene) (PTFE), high density polyethylene (HDPE), low density polyethylene (LDPE), or the like. The tubular sheath 12 defines a longitudinal axis 62, which extends from a proximal end 64 of the tubular sheath 12 to a distal end 66 of the tubular sheath 12. The tubular sheath 12 includes a longitudinal slit 60 that extends substantially parallel to the longitudinal axis 62 of the tubular sheath 12. The longitudinal slit 60 extends from the proximal end 64 of the tubular sheath 12 to the distal end 66 of the tubular sheath 12. The longitudinal slit 60 separates the tubular sheath 12 into a first side 68 and a second side 70, as described above.

As depicted in FIG. 2A, the tubular sheath 12 may include a proximal flare 72, such that the proximal end 64 of the tubular sheath 12 may have a greater terminal radius 78 than a middle section of the tubular sheath 12. The proximal flare 72 may facilitate proximal sliding of the tubular sheath 12 over the catheter 16 (FIGS. 1A-1D). The tubular sheath 12 may further include a distal flare 74, such that a distal end 66 of the tubular sheath 12 may have a greater radius than the middle section of the tubular sheath 12. The distal flare 74 may be configured to facilitate distal sliding of the tubular sheath 12 along the catheter 16. For example, the terminal radius 82 of the distal flare 74 may be greater than an outer radius of the introducer sheath 22 (FIG. 1A) such that the distal flare 74 may be advanced at least partially over the introducer sheath 22. Alternatively, the terminal radius 82 of the distal flare 74 may be smaller than an inner radius of the proximal end of the introducer sheath 22 such that a distal end 66 of the tubular sheath 12 may be inserted into the introducer sheath 22 and therein aid with the introduction of the expandable balloon 14 into the introducer sheath 22. In some examples, an angle 76 (e.g., an angle relative to the longitudinal axis 62) and terminal radius 78 of the proximal flare 72 may be substantially similar to an angle 80 and terminal radius 82 of the distal flare 74. In other examples, the proximal flare 72 may have a different angle 76 or terminal radius 78 than the distal flare 74. In certain examples, the tubular sheath 12 may include a proximal flare 72 but not a distal flare 74, or vice versa.

FIG. 2B is a conceptual and schematic diagram illustrating a cross-sectional view of the tubular sheath 12 taken at the cross-sectional plane 84. As depicted in FIG. 2B, longitudinal slit 60 may cut entirely through the wall of the tubular sheath 12. For examples, the longitudinal slit 60 may cut from an outer surface 86 of the wall of the tubular sheath 12 to an inner surface 88 of the wall of the tubular sheath 12. In other examples (not depicted), the longitudinal slit 60 may cut substantially through the tubular sheath 12, but leave a relatively small "bridge" between the two sides 68, 70 of the tubular sheath 12.

The inner surface 88 of the tubular sheath 12 may be configured to be lubricious to reduce friction between the inner surface 88 and the expandable balloon 14. In some examples, the inner wall 88 may be treated with or include a lubricious coating, such as a hydrophilic coating, a PTFE coating, or a HDPE coating. For example, the majority of the tubular sheath 12 may be made of LDPE, while the inner surface 88 is coated with a hydrophilic coating, PTFE, HDPE, or another lubricious, biocompatible material. Alternatively, the entirety of the tubular sheath 12 may be made of PTFE, HDPE, or another lubricious, biocompatible material. Configuring the inner surface 88 of the tubular sheath 12 to be lubricious may reduce the likelihood of the tubular sheath 12 physically damaging a housed expandable balloon 14 or removing some of the drug coating on an external surface 48 of a housed expandable balloon 14.

The inner surface 88 of the tubular sheath 12 defines an inner lumen 90 of the tubular sheath 12. The inner lumen 90 is configured to house the expandable balloon 14. In some examples, cross-sectional dimensions of the inner lumen 90 defined by the tubular sheath 12 may be substantially constant along the longitudinal axis 62 of the tubular sheath 12. In other examples, cross-sectional dimensions of the inner lumen 90 as measured along the longitudinal axis 62 of the tubular sheath 12 may vary along the length of the tubular sheath 12 (e.g., due to proximal and distal flares 72 and 74).

In some examples, the tubular sheath 12 may include a flexing axis 92. The flexing axis 92 may be located substantially directly opposite from (e.g., about 180° away from) the longitudinal slit 60. Similar to the longitudinal slit 60, the flexing axis 92 may extend from a proximal end 64 of the tubular sheath 12 to a distal end 66 of the tubular sheath 12. The flexing axis 92 may be configured to enable the tubular sheath 12 to move from a closed configuration 94 (e.g., as depicted in FIGS. 2A and 2B where the two sides 68, 70 of the tubular sheath 12 are near each other) to an open configuration 96 (e.g., as depicted in FIG. 2C where the two sides 68, 70 of the tubular sheath 12 are splayed apart). When the tubular sheath 12 is in the closed configuration 94, the tubular sheath 12 may be configured to house the expandable balloon 14 and to be retained upon a catheter 16. Conversely, when the tubular sheath 12 is in the open configuration 96, the tubular sheath 12 may be configured to expose the inner lumen 90 of the tubular sheath 12 such that the tubular sheath 12 is placeable upon or removable from the catheter 16 and exposes the expandable balloon 14.

In some examples, the flexing axis 92 is a crease along the tubular sheath 12 along which the tubular sheath may flex as the two sides 68, 70 of the tubular sheath 12 actuate to bring the tubular sheath 12 from a closed configuration 94 into an open configuration 96. In some examples, the flexing axis 92 may enable the two sides 68, 70 to flex 180° or more around the flexing axis 92 to expose the inner lumen 90 of the tubular sheath 12. In other examples, the flexing axis 92 may be configured to enable relatively less rotation, enabling the two sides 68, 70 of the tubular sheath 12 to only flex 90° away from each other around the flexing axis 92, for example. However, in certain examples, the tubular sheath 12 may not include a flexing axis 92, such that the entirety of both sides 68, 70 of the tubular sheath 12 absorb some stress as the tubular sheath 12 deforms or stretches out into the open configuration 96. Whether the tubular sheath 12 includes or omits the flexing axis 92 may depend on, for example, a flexibility of the materials from which the tubular sheath 12 is formed, or how the tubular sheath is formed (e.g., from a single tube cut open or from two halves joined along the flexing axis). Either way, the tubular sheath 12 is configured to enable sufficient flexing opposite the longitudinal slit 60 to enable the tubular sheath 12 to be removed from a catheter 16.

Though the tubular sheath 12 is discussed and depicted throughout this disclosure as tubular in shape for purposes of clarity and illustration, it is to be understood that any substantially tubular shape that is capable of substantially enclosing an expandable balloon 14 is within the scope of this disclosure. For example, the tubular sheath 12 may be configured to have a changing diameter along the longitudinal axis 62 of the tubular sheath 12. Additionally, or alternatively, the cross-section of the tubular sheath 12 may be, for example, oblong, egg, or diamond-shaped through a portion or the entirety of the length of the tubular sheath 12.

The tubular sheath 12 is retained in the closed configuration 94 by a retaining member 98. The retaining member 98 may be a physical component as discussed herein that is arranged on and engages with both sides 68, 70 of the tubular sheath 12 (on either side of the longitudinal slit 60). The retaining member 98 may be configured to retain the tubular sheath 12 in the closed configuration 94 until the expandable balloon 14 already has been or is about to be inserted into the introducer sheath 22, as discussed in more detail below.

Figure 3:
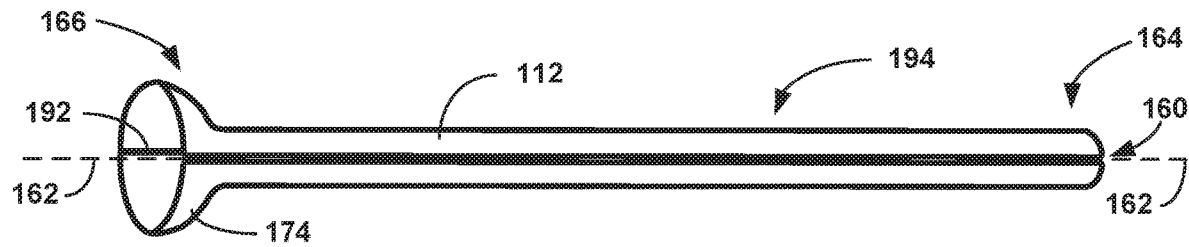
FIG. 3 is a conceptual and schematic diagram illustrating a side view of another example tubular sheath.

FIG. 3 is a conceptual and schematic diagram illustrating a side view of an example tubular sheath 112. The tubular sheath 112 may be substantially similar to the tubular sheath 12 of FIGS. 1A-2B, though as depicted, the tubular sheath 112 only includes an outward distal flare 174 rather than both a proximal 72 and distal flare 74. In other examples the tubular sheath 112 may have both a proximal 72 and distal flare 74 as in tubular sheath 12, or the tubular sheath 112 may have only a proximal flare, or may omit flares. The tubular sheath 112 includes a longitudinal slit 160 that extends from a proximal end 164 of the tubular sheath 112 to a distal end 166 of the tubular sheath 112. The longitudinal slit 160 runs substantially parallel to a longitudinal axis 162 of the tubular sheath 112. The tubular sheath 112 may include a flexing axis 192 substantially similar to the flexing axis 92 as described above, or may omit the flexing axis 192. As depicted in FIG. 3, the tubular sheath 112 is in the closed configuration 194.

Figure 4A:
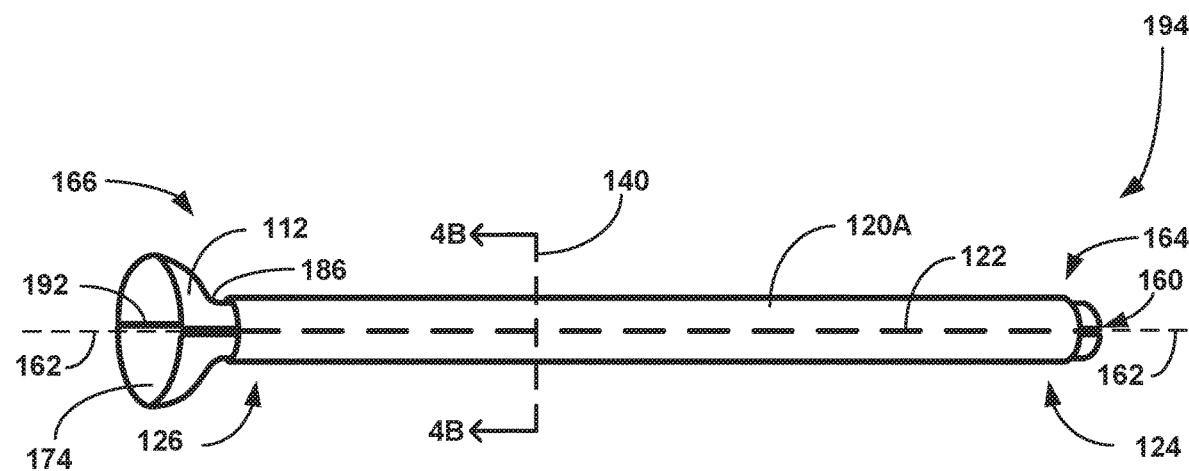
FIGS. 4A and 4B are conceptual and schematic diagrams illustrating views of the tubular sheath of FIG. 3 retained by a first example retaining member, including a side view (FIG. 4A) and a cross-sectional view of the tubular sheath and first example retaining member of FIG. 3 taken along cut plane 140 (FIG. 4B).

FIGS. 4A-8B are conceptual and schematic diagrams illustrating side and cross-sectional views of the tubular sheath 112 of FIG. 3 with various example retaining members 98. The retaining member 98 may be a protective sleeve 120A, 120B, 120C (collectively, "protective sleeves 120") extending from a proximal end 164 of the tubular sheath 112 to a distal end 166 of the tubular sheath 112. Protective sleeves 120 may be configured to cover substantially all of the tubular sheath 112. In some examples, protective sleeves 120 may be configured to expose (e.g., not cover) some of the proximal end 164 and/or distal end 166 of the tubular sheath 112, as depicted in FIG. 4A. Further, in some examples, protective sleeves 120 may be configured to not cover outward flared ends (e.g., distal flare 174) of the tubular sheath 112. Conversely, in other examples, protective sleeves 120 may be configured to cover substantially all of an outer surface 186 of the tubular sheath 112, including a distal flare 174 of the tubular sheath 112.

Figure 4B:
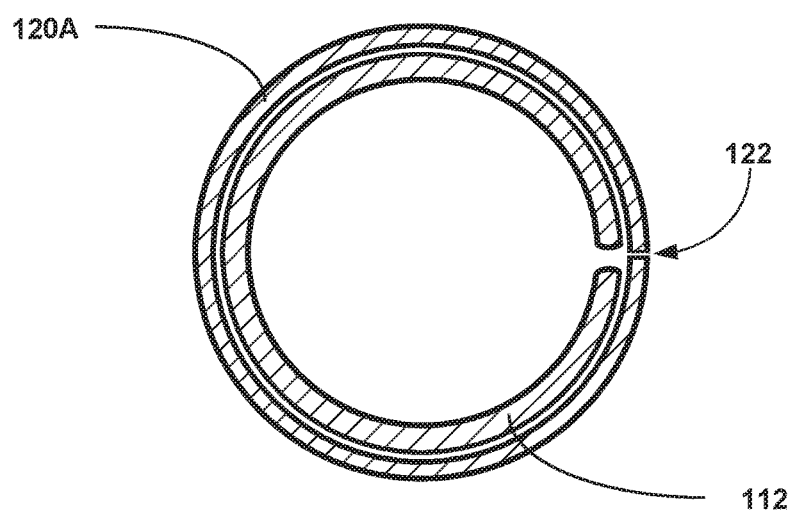

In some examples, protective sleeves 120 may be formed of a polymer material, or another material suitable to provide column stiffness to the tubular sheath 112 (e.g., stiffness for supporting the expandable balloon 14 during insertion of the expandable balloon 14 into the introducer sheath 22). For example, the protective sleeve 120A may be a relatively thin film with a plurality of longitudinal perforations 122. Each perforation 122 of the plurality of longitudinal perforations 122 may be configured to cut substantially through one side of the protective sleeve 120A. For example, FIG. 4B illustrates a cross-sectional view taken along cut plane 140 of a protective sleeve 120A that includes perforations 122. Cut plane 140 intersects with a perforation 122. As depicted in FIG. 4B, the perforation 122 cuts substantially through one side of the protective sleeve 120A.

The perforations 122 may be configured to extend from a proximal end 124 of the protective sleeve 120A to a distal end 126 of the protective sleeve 120A. While in FIG. 4A the perforations 122 are depicted as being substantially parallel with the longitudinal axis 162 of the tubular sheath 112 for purposes of clarity, in other examples the perforations 122 may be configured to be at an angle relative to the longitudinal axis 162 of the tubular sheath 112 or to spiral around the longitudinal axis 162 of the protective sleeve 120A. Further, while in FIG. 4A a single line of perforations 122 is depicted for purposes of clarity, in other examples, the protective sleeve 120A may include two or more lines of perforations 122 extending along the protective sleeve 120A. In examples in which the protective sleeve 120A defines a single line of perforations 122, the single line of perforations 122 may substantially align with the longitudinal slit 160 of the tubular sheath 112 as depicted. Aligning the perforations 122 with the longitudinal slit 160 may provide advantages in identifying, orienting, and/or otherwise handling the protective sleeve 120A, the tubular sheath 112, and or the catheter 16.

The protective sleeve 120A may be configured to be initially slid onto the tubular sheath 112 and afterwards split along the plurality of longitudinal perforations 122. For example, a clinician may grab the proximal 124 or distal end 126 of the protective sleeve 120A adjacent to the plurality of longitudinal perforations 122 and pull radially away from the tubular sheath 112 in order to split the protective sleeve 120A. The protective sleeve 120A may be configured to split along the perforations 122 in response to a force above a threshold force being exerted upon the protective sleeve 120A. The threshold force may be a force that is higher than a nominal force that may be unintentionally exerted upon the protective sleeve 120A while also being less than a maximum force that an adult could exert upon the protective sleeve 120A. Put differently, the threshold force may be a force that is relatively easy for an adult to intentionally apply to the protective sleeve 120A while being relatively difficult to unintentionally apply while handling the medical device 10. In certain examples, the protective sleeve 120A may include a tab (not depicted) attached to the proximal end 124 of the protective sleeve 120A to facilitate the removal of the protective sleeve 120A from the tubular sheath 112. In other examples, a tab may alternatively or additionally be connected to the distal end 126 of the protective sleeve 120A.

Thus, when located on the tubular sheath 112, the protective sleeve 120A with perforations 122 maintains the tubular sheath 112 in the closed configuration 194. When the plurality of perforations 122 are stressed, the protective sleeve 120A may break open along the perforations 122. Once the protective sleeve 120A is broken open, the tubular sheath 112 is no longer retained in the closed configuration 194, enabling the tubular sheath 112 to be converted to the open configuration. Once in the open configuration, the tubular sheath 112 may be removed from the catheter 16. In this way, the protective sleeve 120A may be configured to retain the tubular sheath 112 in the closed configuration 194 while also being configured to be removable, enabling the tubular sheath 112 to convert to the open configuration.

Figure 5A:
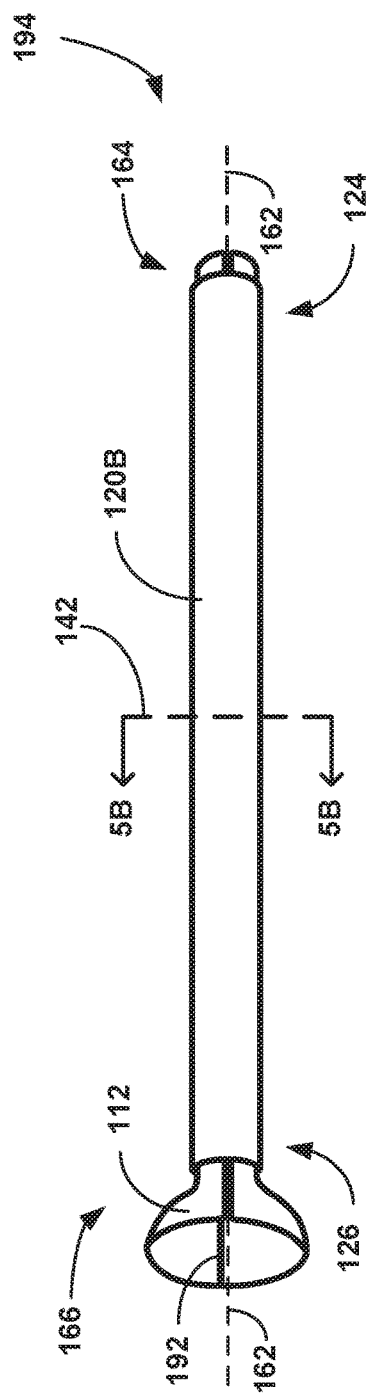
FIGS. 5A and 5B are conceptual and schematic diagrams illustrating views of an example tubular sheath retained by an example retaining member, including a side view (FIG. 5A) and a cross-sectional view of the tubular sheath and retaining member of FIG. 5A taken along cut plane 142 (FIG. 5B).
Figure 5B:
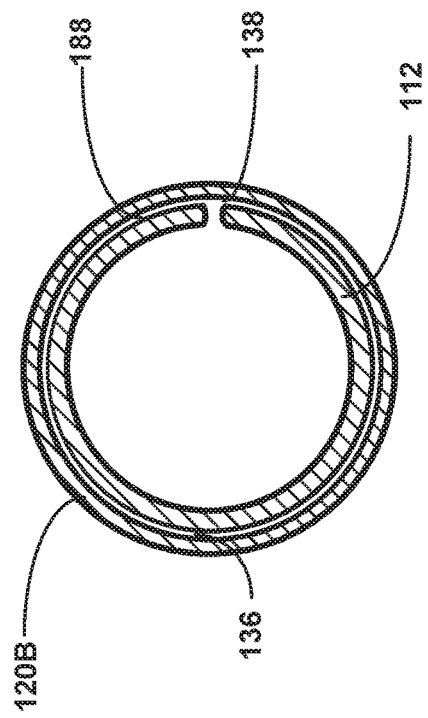

As depicted in FIGS. 5A and 5B, the protective sleeve 120B may be formed from a heat-shrinkable film. When the protective sleeve 120B is formed from the heat-shrinkable film, the protective sleeve 120B may omit the plurality of longitudinal perforations 122. Rather, the heat-shrinkable protective sleeve 120B may be loosely placed over the tubular sheath 112 and exposed to heat above a threshold shrinking temperature until the heat-shrinkable film shrinks to the size depicted in the cross-sectional view depicted in FIG. 5B taken at cut plane 142 shown in FIG. 5A. In some examples, the protective sleeve 120B may define substantially zero space 136 between the protective sleeve 120B and the tubular sheath 112, such that the protective sleeve 120B shrinks substantially directly to the outer surface 186 of the tubular sheath 112. In this shrunken state, the protective sleeve 120B is configured to retain the tubular sheath 112 in the closed configuration 194. The heat-shrinkable protective sleeve 120B may be configured to be tearable by hand by a clinician, such as by grabbing the proximal 124 or distal end 126 of the protective sleeve 120B and pulling radially away from the tubular sheath 112. For example, the protective sleeve 120B may be configured to be tearable in response to a force above a threshold force (as discussed above) being exerted upon the protective sleeve 120B. In some embodiments, the protective sleeve 120B may be cut to enable removal, such as cutting the entire protective sleeve 120B from end-to-end, or by cutting a portion of the protective sleeve 120B and then tearing the protective sleeve 120B from the cut portion (i.e., using the cut to make the tearing easier. In certain examples, the protective sleeve 120B may include a tab (not depicted) attached to the proximal end 124 of the protective sleeve 120B to facilitate the removal of the protective sleeve 120B from the tubular sheath 112. In other examples, a tab may alternatively or additionally be connected to the distal end 126 of the protective sleeve 120B.

Thus, when located on tubular sheath 112, the heat-shrinkable protective sleeve 120B is configured to maintain the tubular sheath 112 in the closed configuration 194. When the protective sleeve 120B is stressed, torn, or cut, the protective sleeve 120A may break open. Once the protective sleeve 120B is broken open, the tubular sheath 112 is no longer retained in the closed configuration 194, enabling the tubular sheath 112 to convert to the open configuration. Once in the open configuration, the tubular sheath 112 may be removed from the catheter 16. In this way, the protective sleeve 120B is configured to retain the tubular sheath 112 in the closed configuration 194 while also being configured to be removable, enabling the tubular sheath 112 to be converted to the open configuration.

Figure 6A:
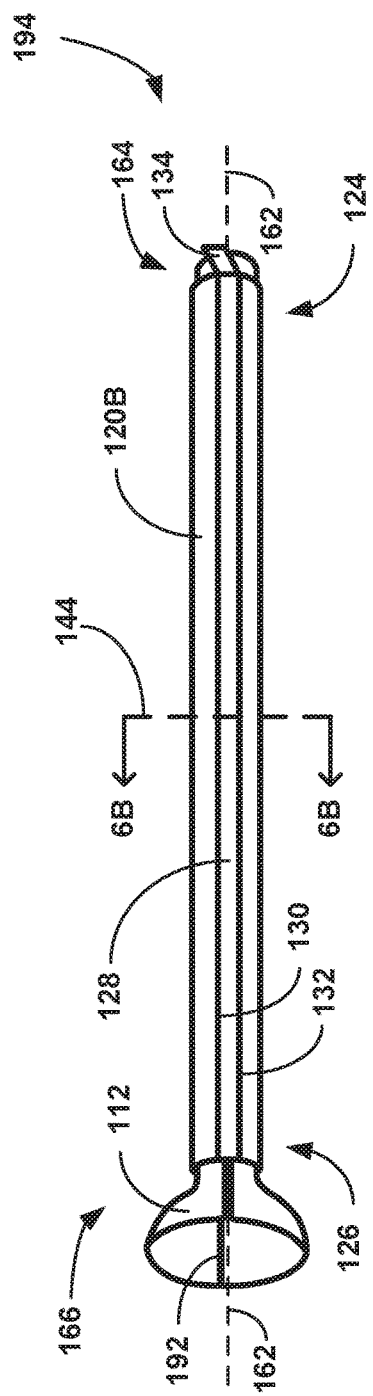
FIGS. 6A and 6B are conceptual and schematic diagrams illustrating views of a tubular sheath retained by an example retaining member, including a side view (FIG. 6A) and a cross-sectional view of the tubular sheath and retaining member of FIG. 6A taken along cut plane 144 (FIG. 6B).
Figure 6B:
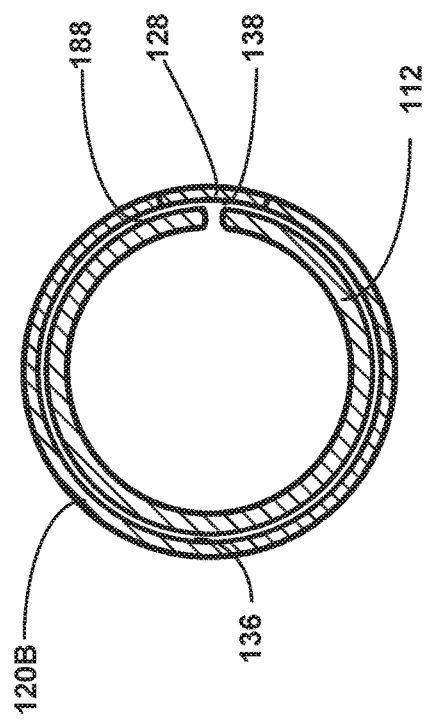

Alternatively, as depicted in FIGS. 6A and 6B, a protective sleeve 120C may be configured to be longitudinally peelable. For example, the protective sleeve 120C may be configured to be peeled off of the tubular sheath 112 from a proximal end 124 of the protective sleeve 120C to a distal end 126 of the protective sleeve 120C, or vice versa. The protective sleeve 120C may be configured to be peelable as a result of a longitudinal weakness of the protective sleeve 120C that enables the protective sleeve 120C to be peeled in response to a force above a threshold force as discussed herein that is exerted upon the protective sleeve 120C.

For example, a protective sleeve 120C that is peelable may include a peelable strip 128 that extends from a proximal end 124 of the protective sleeve 120C to a distal end 126 of the protective sleeve 120C. The peelable strip 128 is configured to peel away from the rest of the protective sleeve 120C. The peelable strip 128 may be configured to peel away due to a relatively weak bond between the peelable strip 128 and adjacent portions of the protective sleeve 120C, a longitudinal cut along one or both sides 130, 132 of the peelable strip 128, or due to other equivalent techniques that would impair bonding of the peelable strip 128 to adjacent portions of the protective sleeve 120C while enabling the protective sleeve 120C to retain the tubular sheath 112 in the closed configuration 194. In certain examples, the protective sleeve 120C may include a tab 134 attached to the proximal end 124 of the protective sleeve 120C to facilitate the peeling removal of the protective sleeve 120C from the tubular sheath 112. In other examples, a tab 134 may alternatively or additionally be connected to the distal end 126 of the protective sleeve 120C.

Thus, when located on tubular sheath 112, the peelable protective sleeve 120C is configured to maintain the tubular sheath 112 in the closed configuration 194. When the protective sleeve 120C is stressed (e.g., along the peelable strip 128), the protective sleeve 120C will break open. Once the protective sleeve 120C is broken open, the tubular sheath 112 is no longer retained in the closed configuration 194, enabling the tubular sheath 112 to convert to the open configuration. Once in the open configuration, the tubular sheath 112 may be removed from the catheter 16. In this way, the protective sleeve 120C is configured to retain the tubular sheath 112 in the closed configuration 194 while also being configured to be removable, enabling the tubular sheath 112 to be converted to the open configuration. Further, in some examples, the peelable strip 128 may be configured to be predictable/controllably peeled in response to a predetermined force, enabling a clinician to controllably open the protective sleeve 120C and therein convert the tubular sheath 112 to an open configuration in a steady fashion. This may enable the clinician to maintain portions of the tubular sheath 112 that surround the portions of the expandable balloon 14 not yet advanced into the introducer sheath 22 in a closed configuration 194, while converting portions of the tubular sheath 112 that formerly surrounded portions of the expandable balloon 14 within the introducer sheath 22 or the vasculature 24 of the patient 26 in an open configuration. This may facilitate advancing the expandable balloon 14 into the introducer sheath 22 while protecting the expandable balloon 14 with the tubular sheath 112.

FIG. 6B is a conceptual and schematic diagram illustrating a cross-sectional view of the protective sleeve 120C on the tubular sheath 112 taken at the cross-sectional cut-plane 144 (shown in FIG. 6A). The protective sleeve 120C may be configured such that there is relatively little or functionally no space 136 between an inner surface 138 of the protective sleeve 120C and an outer surface 186 of the tubular sheath 112. In some examples, the protective sleeve 120C may be configured to define just enough space 136 between the protective sleeve 120C and the tubular sheath 112 such that the protective sleeve 120C does not press upon the tubular sheath 112 and reduce a radius of the tubular sheath 112.

As depicted in FIG. 6B, tubular sheaths 112 may have walls that are relatively thicker in cross-section than walls of the protective sleeves 120A, 120B, 120C. Configuring the walls of a tubular sheath 112 to be relatively thicker may result in the tubular sheath 112 being more structurally robust while configuring protective sleeves 120A, 120B, 120C to be relatively easy to remove from the tubular sheath 112.

FIGS. 7A and 7B depict two side views of the tubular sheath 112 of FIG. 3 and a protective sleeve 120D, with FIG. 7B rotated 90° around the longitudinal axis 162 of the tubular sheath 112 relative to FIG. 7A. As depicted in FIGS. 7A and 7B, the protective sleeve 120D defines a notched groove 150. The notched groove 150 may be configured to extend longitudinally in from a proximal end 124 of the protective sleeve 120D parallel to the longitudinal axis 162 of the tubular sheath 112. In some examples, the protective sleeve 120D may be configured to alternatively or additionally include a notched groove 150 that extends in from a distal end 126 of the protective sleeve 120D. The notched groove 150 may be configured to substantially align with (e.g., align with or nearly align with) the longitudinal slit 160 in the tubular sheath 112 such that the notched groove 150 visually exposes the longitudinal slit 160.

In some examples, the notched groove 150 of this protective sleeve 120D may be combined with the perforations 122 of the perforated protective sleeve 120A, the heat-shrinkable aspect of the heat shrinkable protective sleeve 120B, and/or the peelable strip 128 of the peelable protective sleeve 120C. Combining the notched groove 150 with features of the other protective sleeves 120A, 120B, 120C discussed herein may further configure those protectives sleeves 120 to visually expose the longitudinal slit 160 with the notched groove 150, potentially providing advantages in identifying, orienting, and/or otherwise handling the protective sleeves 120, respective tubular sheaths 112, and or the respective catheters 16. The notched groove 150 may also further enable the removal of the protective sleeve 120D, for example, by providing tab-like areas for the clinician to grasp, and/or by providing a notch than may act as a starting point to tear or slit the protective sleeve 120D.

Figure 8A:
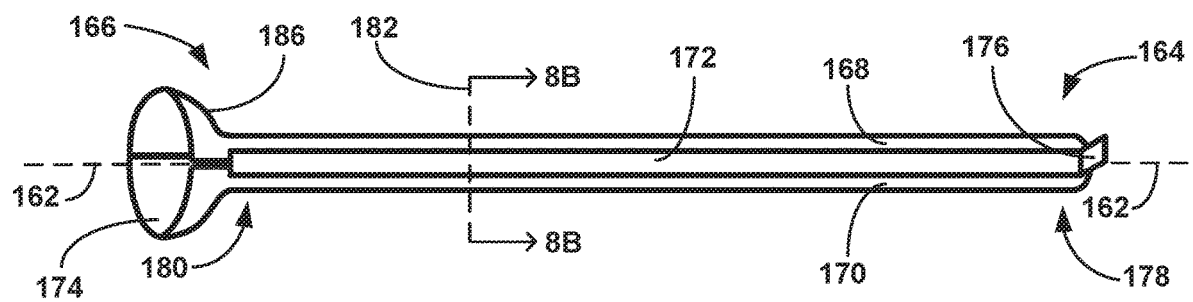
FIGS. 8A and 8B are conceptual and schematic diagrams illustrating various views of a tubular sheath retained by an example retaining member, including a side view (FIG. 8A) and a cross-sectional view of the tubular sheath and third example retaining member of FIG. 8A taken along cut plane 182 (FIG. 8B).
Figure 8B:
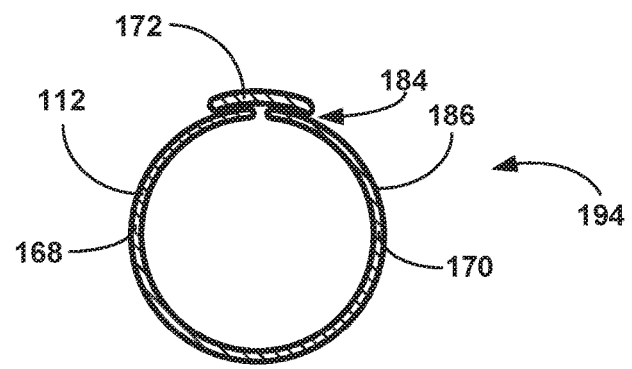

FIG. 8A is a conceptual and schematic diagram illustrating a side view of the tubular sheath 112 of FIG. 3 with an example retaining member 98 that includes a strip of adhesive 172. FIG. 8B is a conceptual and schematic diagram illustrating a cross-sectional view of the of the tubular sheath 112 with the strip of adhesive 172 taken a cut plane 182 (shown in FIG. 8A). In the example of FIGS. 8A and 8B, the retaining member 98 includes a strip of adhesive 172 that extends from a location adjacent to a proximal end 164 of the tubular sheath 112 to a location adjacent to a distal end 166 of the tubular sheath 112. The adhesive strip 172 may be configured to substantially cover the longitudinal slit 160 from a location adjacent to the proximal end 164 of the tubular sheath 112 to a location adjacent to the distal end 166 of the tubular sheath 112. The adhesive strip 172 is configured to cover the longitudinal slit 160 such that the adhesive strip 172 adheres to both sides 168, 170 of the tubular sheath 112 across the longitudinal slit 160. In some examples, the adhesive strip 172 may be configured to expose (e.g., not cover) some of the longitudinal slit 160 adjacent to the proximal end 164 and/or adjacent to the distal end 166 of the tubular sheath 112, as depicted in FIG. 8A. Further, as depicted, in some examples, the adhesive strip 172 may be configured to not cover outward flared ends (e.g., distal flare 174). Conversely, in other examples, the adhesive strip 172 may be configured to cover substantially all of an outer surface 186 of the tubular sheath 112, including a distal flare 174 of the tubular sheath 112. The adhesive strip 172 may be configured to be pulled off of the tubular sheath 112 in response to a force above a threshold force as discussed herein. A user such as a clinician may exert the force upon a proximal end 178 or distal end 180 of the adhesive strip 172. In some examples, the adhesive strip 172 may include a tab 176 that extends radially away from the tubular sheath 112 to facilitate the application of the force upon the adhesive strip 172. For example, the tab 176 may be gripped by a clinician and pulled from the tubular sheath 112 in a direction which is distal and radially outward from the tubular sheath 112.

FIG. 8B is a conceptual and schematic diagram illustrating a cross-sectional view of the of the tubular sheath 112 with the strip of adhesive 172. The cross-section is looking along the longitudinal axis 162 at the cross-sectional cut plane 182 (FIG. 8A). As depicted in FIG. 8B, an inner surface 184 of the adhesive strip 172 is pressed against and adhered to the outer surface 186 of the tubular sheath 112. The adhesive of the adhesive strip 172 may be any adhesive that is configured to adhere to both sides 168, 170 of the tubular sheath 112 to retain the tubular sheath 112 in the closed configuration 194, such a silicone adhesive, an acrylate, or an epoxy. Further, in some embodiments, the adhesive strip 172 may include a tape backing (not shown), wherein the adhesive is located between the outer surface 186 of the tubular sheath 112 and the tape backing.

Thus, the adhesive strip 172 may be configured to maintain the tubular sheath 112 in the closed configuration 194. When adhesive strip 172 is removed, the tubular sheath 112 is no longer retained in the closed configuration 194, enabling the tubular sheath 112 to convert to the open configuration. Once in the open configuration, the tubular sheath 112 may be removed from the catheter 16. In this way, the adhesive strip 172 is configured to retain the tubular sheath 112 in the closed configuration 194 while also being configured to be removable, enabling the tubular sheath 112 to be converted to the open configuration. Further, in some examples, the adhesive strip 172 may be configured to be predictable/controllably peeled in response to a predetermined force, enabling a clinician to remove the adhesive strip 172 and therein convert the tubular sheath 112 to an open configuration in a steady fashion. This may enable the clinician to maintain portions of the tubular sheath 112 that surround the portions of the expandable balloon 14 not yet advanced into the introducer sheath 22 in a closed configuration 194, while converting portions of the tubular sheath 112 that formerly surrounded portions of the expandable balloon 14 within the introducer sheath 22 or the vasculature 24 of the patient 26 in an open configuration. This may facilitate advancing the expandable balloon 14 into the introducer sheath 22 while protecting the expandable balloon 14 with the tubular sheath 212.

Figure 9A:
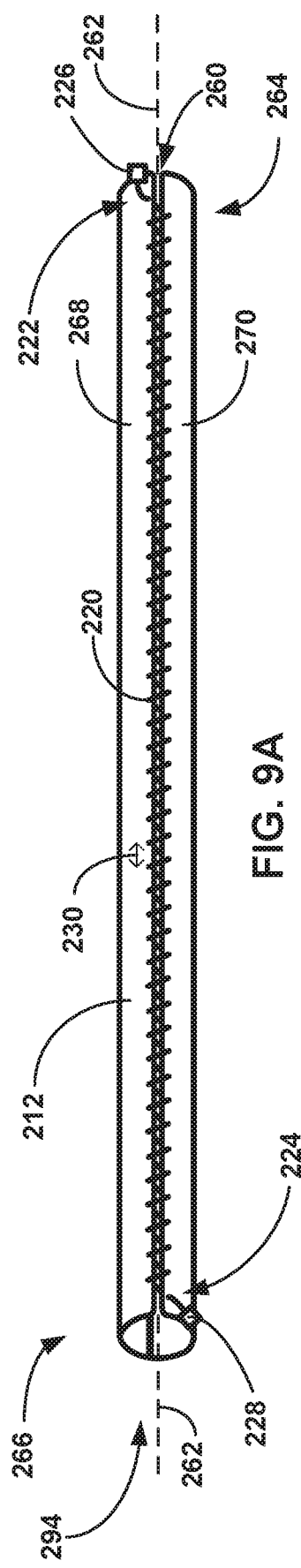
FIGS. 9A and 9B are conceptual and schematic diagrams illustrating side views of example tubular sheaths with suture retaining members.

In some examples, rather than a protective sleeve 120 or an adhesive strip 172, a retaining member 98 may include a stitch or suture. For example, FIG. 9A is a conceptual and schematic diagram illustrating a side view of an example tubular sheath 212 with an example retaining member that includes a suture 220. The suture 220 may be made with a polymer or textile (e.g., expanded polytetrafluoroethylene (ePTFE) or silk). The tubular sheath 212 may have a longitudinal slit 260 that bisects two sides 268, 270 of the tubular sheath 212. The tubular sheath 212 may be substantially similar to the tubular sheath 12 of FIGS. 1A-2B and the tubular sheath 112 of FIGS. 3-8B, though the tubular sheath 212 is not depicted with an outward flare at either a proximal end 264 or a distal end 266 of the tubular sheath 212. In the example of FIG. 9A, the retaining member 98 is a suture 220 extending from a location adjacent to a proximal end 264 of the tubular sheath 212 to a location adjacent to a distal end 266 of the tubular sheath 212. The suture 220 may be configured to stitch together the two sides 268, 270 of the tubular sheath 212, retaining the tubular sheath 212 in the closed configuration 294. In some examples, the longitudinal slit 260 and the suture 220 may be configured to be substantially parallel with the longitudinal axis 262 of the tubular sheath 212.

In some examples, the suture 220 may be configured to stitch together the two sides 268, 270 of the tubular sheath 212 across substantially all of the longitudinal slit 260. In some examples, the suture 220 may be configured to leave some portion of the two sides 268, 270 at the proximal end 264 and/or distal end 266 of the tubular sheath 112 unstitched, as depicted in FIG. 9A. Further, in some examples where the tubular sheath 212 includes distal flares or proximal flares as discussed herein, the suture 220 may be configured to not stitch together the two sides 268, 270 along these outward flares. Conversely, in other examples, the suture 220 may be configured to stitch together the two sides 268, 270 of the tubular sheath 212 along nearly all of the longitudinal slit 260, including along a distal flare and proximal flare of the tubular sheath 212.

The suture 220 is configured to be pulled and unraveled from the tubular sheath 212 in response to a force above a threshold force as discussed herein. The force may be exerted upon a proximal end 222 or distal end 224 of the suture 220. In some examples, the suture 220 may include a tab 226 attached to the proximal end 222 of the suture 222 and/or a tab 228 attached to the distal end 224 of the suture 220. The tabs 226, 228 may be configured to facilitate the application of the force above the threshold force upon the suture 220. For example, the proximal tab 226 may be configured to be gripped by a clinician and pulled from the tubular sheath 212 in a direction which is both distal and radially out from the tubular sheath 212 to unravel the suture 220. The suture 220 may be configured to be controllably unraveled, such that a clinician has a degree of control over when a specific portion of suture 220 is unraveled from the tubular sheath 212.

Figure 9B:
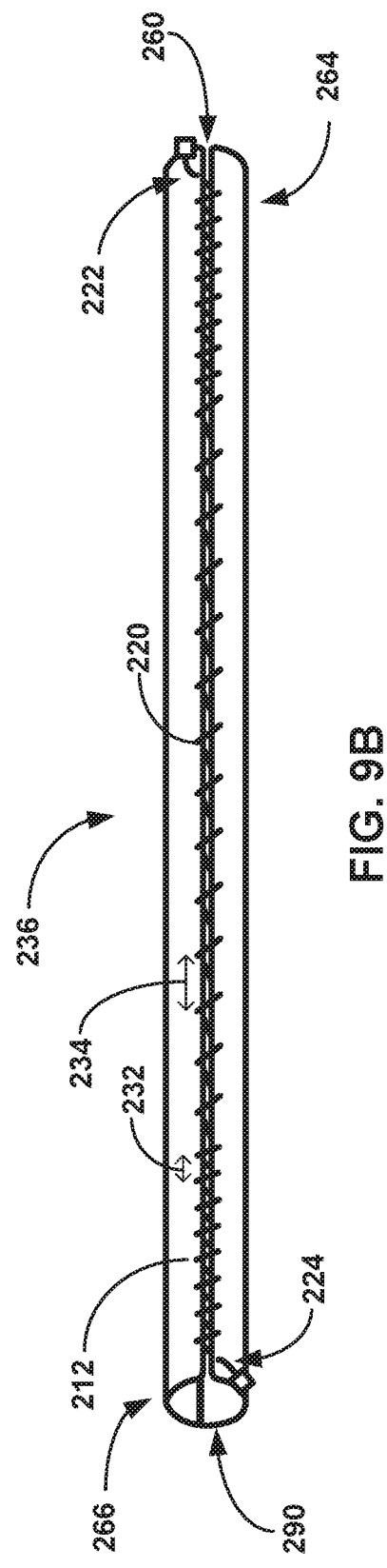

In some examples, the distance 230 between stitches of the suture 220 may be configured to be relatively constant throughout the length of the suture 220 for ease of manufacturing and to enable a constant force to result in a constant unstitching of the suture 220, as shown in FIG. 9A. However, in other examples such as depicted in FIG. 9B, the suture may be configured to include a first distance 232 between stitches of the suture 220 at one location and a second, relatively greater second distance 234 between stitches of the suture 220 at another location. The shorter first distances 232 may enable a clinician to have more control at a specific portion of the tubular sheath 212 in unraveling the suture 220 and exposing the respective portion of the inner lumen 290 of the tubular sheath 212. Conversely, the longer second distances 234 may enable a clinician to unravel a respective portion of the tubular sheath 212 faster in areas where there might be less need for control. As such, the suture 220 may be configured to have "tighter" stitches at a first distance 232 at a distal end 266 (e.g., to have maximum control when inserting an expandable balloon 14 into an introducer sheath 22) and/or a proximal portion 264 of the tubular sheath 212 (e.g., to have maximum control when finally undoing a suture 220 to remove the tubular sheath 212) while having "looser" stitches at a second distance 234 in a middle section 236 of the tubular sheath 212.

Thus, when the suture 220 is engaged with the sides 268 and 270 of the tubular sheath 212, the suture 220 maintains the tubular sheath 212 in a closed configuration. When the suture 220 is unraveled to disengage the suture 220 from the two sides 268 and 270 of the tubular sheath 212, this controllably transitions portions of the tubular sheath 212 to an open configuration. By starting unraveling or removal of the suture 220 from the distal end 266 of the tubular sheath 212 as the expandable balloon 14 is advanced into the introducer sheath 22 (FIG. 1A), the clinician may transition selected amounts of the tubular sheath 212 from the closed configuration to the open configuration. This may enable the clinician to maintain portions of the tubular sheath 212 that surround the portions of the expandable balloon 14 not yet advanced into the introducer sheath in a closed configuration, while converting portions of the tubular sheath 212 that formerly surrounded portions of the expandable balloon 14 within the introducer sheath 22 or the vasculature 24 of the patient 26 in an open configuration. This may facilitate advancing the expandable balloon 14 into the introducer sheath 22 while protecting the expandable balloon 14 with the tubular sheath 212.

Figure 10:
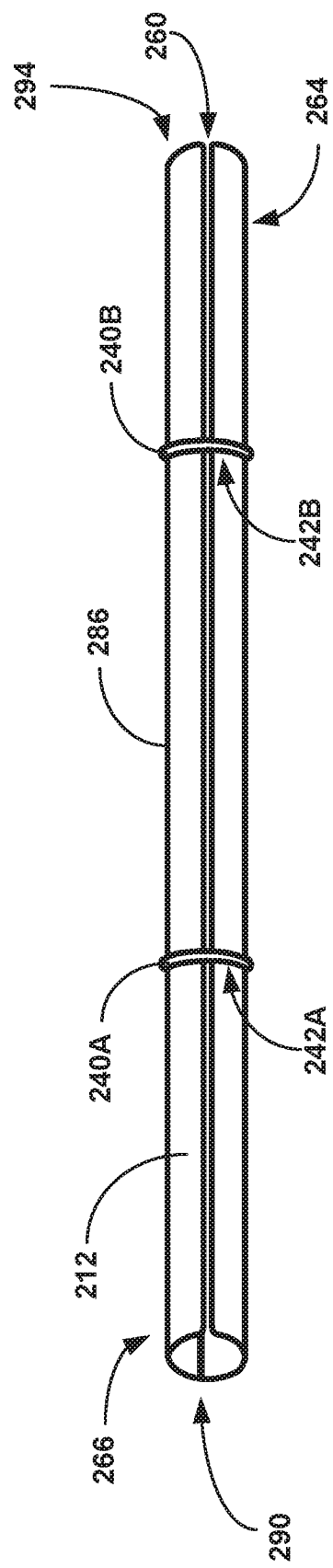
FIG. 10 is a conceptual and schematic diagram illustrating a side view of an example tubular sheath with ring retaining members.

In some examples, rather than a protective sleeve 120, an adhesive strip 172, or a suture 220, a retaining member 98 may include one or more rings. For example, FIG. 10 is a conceptual and schematic diagram illustrating a side views of the example tubular sheath 212 with example retaining members 98. The retaining member 98 may include two rings 240A, 240B (collectively, "rings 240") that may be configured to be independently slideable along a longitudinal length of the tubular sheath 212. The rings 240 are configured to be wrapped around substantially the entirety of the outer surface 286 of the tubular sheath 212 to retain the tubular sheath 212 in the closed configuration 294 as discussed herein. While two rings 240 are depicted in FIG. 10 for purposes of illustration, in other examples a single ring 240 or more than two rings 240 may be used.

The rings 240 may be configured to be slid either proximally or distally off of the tubular sheath 212 to expose the inner lumen 290 of the tubular sheath 212. In other embodiments, the rings 240 may be configured to be broken to be removed from the tubular sheath 212. For example, the rings 240 may be configured with an area of weakness, such as a notch or thinned section of the ring 240 that is relatively easier to break or tear. In some examples, the rings 240 may be configured such that inner surfaces 242A, 242B (collectively, "inner surfaces 242") of the rings 240 have a slight interference fit with the tubular sheath 212 in the closed configuration 294. In such examples, the rings 240 may be configured to be slid proximally or distally in response to a force above a threshold force as discussed herein. The rings 240 may be made from a material that is sufficiently stiff and strong to maintain a shape and retain the tubular sheath 212 in the closed configuration 294. For example, the rings 240 may be metallic, or the rings 240 made from a hard polymer.

Thus, the rings 240 may be configured to be slid proximally and distally along the tubular sheath 112, enabling a clinician to controllably open the tubular sheath 212 by sliding the relevant ring(s) 240 proximally along the tubular sheath 212 to convert the tubular sheath 212 to an open configuration. This may enable the clinician to maintain portions of the tubular sheath 112 that surround the portions of the expandable balloon 14 not yet advanced into the introducer sheath 22 in a closed configuration 194 (e.g., by keeping one or more rings 240 around these portions), while converting other portions of the tubular sheath 212 that formerly surrounded portions of the expandable balloon 14 in an open configuration. This may facilitate advancing the expandable balloon 14 into the introducer sheath 22 while protecting the expandable balloon 14 with the tubular sheath 212.

In some examples, rather than protective sleeves 120, an adhesive strip 172, a suture 220, or one or more rings 240, a retaining member 98 may be a clasp. For example, FIG. 11A is a conceptual and schematic diagram illustrating a side view of an example tubular sheath 312 with an example retaining member 98 that includes a clasp 320. The tubular sheath 312 includes a longitudinal slit 360 that bisects two sides 368, 370 of the tubular sheath 312. The tubular sheath 312 may be configured to have a proximal outward flare 372 as discussed herein. The tubular sheath 312 may be substantially similar to the tubular sheath 12 of FIGS. 1A-2B, the tubular sheath 112 of FIGS. 3-8B, and the tubular sheath 212 of FIGS. 9A-10, though as depicted the tubular sheath 312 has a changing cross-sectional profile. For example, the internal lumen 390 of the tubular sheath 312 may be tapered from a proximal end 364 of the tubular sheath 312 to a distal end 366 of the tubular sheath 312. In the example of FIGS. 11A-11C, the retaining member includes a clasp 320 extending across the longitudinal slit 360 of the tubular sheath 312 to connect the two sides 368, 370 of the tubular sheath 312. The clasp 320 is configured to clasp together the two sides 368, 370 of the tubular sheath 312, retaining the tubular sheath 312 in the closed configuration 394. While one clasp 320 is depicted in FIG. 11A for purposes of illustration, in other examples two or more clasps 320 may be used to retain the tubular sheath 312 in the closed configuration 394.

In some examples, the distal end 366 may include/be connected to a Luer fitting 340 to receive/be received by the introducer sheath 22. The Luer fitting 340 may include a slit, crack, or other structural weakness to configure the Luer fitting 340 to be controllably broken open by a clinician (e.g., when the tubular sheath 312 is to be removed from the catheter 16). The structural weakness may substantially align, or be coextensive, with the longitudinal slit 360 of the tubular sheath 312 to enable the removal of the sheath 312 from the catheter in a radially outward direction. In some examples, the longitudinal slit 360 may extend through the Luer fitting 340, such that the longitudinal slit 360 substantially is the structural weakness.

The Luer fitting 340 may include an internal surface 388 on the distal end 366 of the tubular sheath 312 being internally threaded with threads 322. The threads 322 may be interrupted by the longitudinal slit 360. The threads 322 may act as a Luer connector to enable the tubular sheath 312 to connect to a complementary Luer connector on the introducer sheath 22 (FIG. 1A). Configuring the internal surface 388 of the distal end of the tubular sheath 312 to define threads 322 to transform the distal end 366 of the tubular sheath 312 into a Luer connector may enable the tubular sheath 312 to introduce the expandable balloon 14 to the introducer sheath 22 in a more stable manner, therein potentially decreasing an amount of risk of causing physical damage to or contact with the expandable balloon 14. While this configuration is depicted only with the retaining member 98 being shown as a clasp 320, this configuration of the tubular sheath 312 may be used with any of the previously described retaining members 98.

FIGS. 11B and 11C depict cross-sectional views of a portion of tubular sheath 312 that includes the clasp 320 as viewed proximally from the cross-sectional cut plane 324 (FIG. 11A). The clasp 320 is configured to engage a mating element 326 to retain the two sides 368, 370 across the longitudinal slit 360. The clasp 320 may be attached to one side 368 of the tubular sheath 312 while the mating element 326 is attached to the other side 370 of the tubular sheath 312. The mating element 326 may be configured to be fixedly attached to the tubular sheath 312, such that the mating element 326 is not configured to move relative to the tubular sheath 312. Conversely, the clasp 320 may be attached in a hinged or pivoting fashion to the tubular sheath 312 to enable the clasp 320 to pivot in relation to the tubular sheath 312 as depicted in FIGS. 11B and 11C. Configuring the tubular sheath 312 to include a retaining member 98 that can repeatedly engage and disengage the two sides 368, 370 of the tubular sheath 312 may enable the tubular sheath 312 to be repeatedly placed upon and removed from the catheter 16, providing procedural flexibility to a clinician.

For example, configuring the tubular sheath 312 to be repeatedly converted between an open configuration and closed configuration 394 may enable the tubular sheath 312 to be converted from an open configuration to a closed configuration 394 over the catheter 16 (e.g., such that the catheter 16 is within the lumen 390 of the tubular sheath 312) proximal to the expandable balloon 14. Such a configuration may be advantageous where a catheter 16 and an expandable balloon 14 come equipped with a non-openable storage sheath (e.g., come packaged from a manufacturing plant in this fashion). It may be disadvantageous to slide the storage sheath off the expandable balloon 14/catheter 16 distally before sliding a tubular sheath 12/112/212/312 onto the expandable balloon 14 proximally, as such a method may leave the expandable balloon 14 temporarily uncovered. Leaving the expandable balloon 14 temporarily uncovered may increase the chances of the expandable balloon and/or a drug coating of the expandable balloon 14 being physically damaged (e.g., as a clinician/object may touch the uncovered expandable balloon 14 during this time). Further, it may be disadvantageous to proximally slide the non-openable storage sheath on the catheter 16 with the tubular sheath 12/112/212/312 as the tubular sheath 12/112/212/312 is being distally slid onto the expandable balloon 14, as such a method may reduce the operation length of the catheter 16 by at least the longitudinal length of the storage sheath. Thus, configuring the tubular sheath 312 to repeatedly convert between open and closed configurations 394 may facilitate a storage sheath being removed without either exposing the expandable balloon 14 or reducing the operational length of the catheter 16 by the longitudinal length of the storage sheath.

Figure 12:
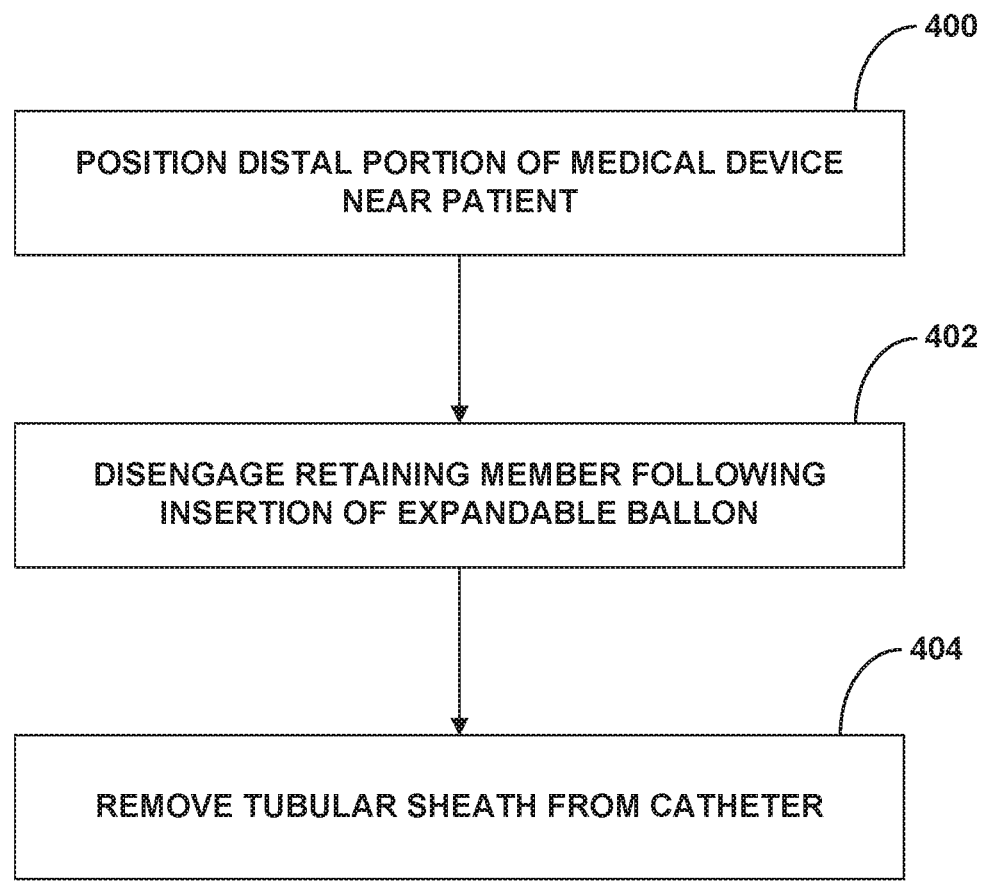
FIG. 12 is a flow diagram illustrating an example method of inserting an expandable balloon into a patient using a tubular sheath

FIG. 12 is a flow diagram illustrating a method of inserting an expandable balloon 14 using a tubular sheath 12. Although the technique of FIG. 12 will be described with reference to the medical device 10 and other components illustrated in FIGS. 1A-1D, it will be appreciated that the technique of FIG. 12 may be used with any of the medical devices described herein. The technique of FIG. 12 includes a clinician positioning a distal portion of a medical device 10 near a patient 26 (400). The medical device 10 may include an expandable balloon 14 that is housed by a tubular sheath 12 and attached to a catheter 16. In some examples, the distal portion of the medical device 10 may be positioned near an introducer sheath 22 that is inserted within the patient 26. The introducer sheath 22 may terminate within vasculature 24 of the patient 26.

A clinician may disengage the retaining member 98 from one or both sides 68, 70 of the tubular sheath 12 (402). A clinician may disengage the retaining member 98 from one or both sides 68, 70 of the tubular sheath 12 to convert the tubular sheath 12 into the open configuration 96. In some examples, a clinician may disengage the retaining member 98 from one or both sides 68, 70 of the tubular sheath 12 in portions or sections, such that the lumen 90 of the tubular sheath 12 is exposed at a distal end 66 of the tubular sheath 12 but not exposed at a proximal end 64 of the tubular sheath 12 (e.g., when the retaining member 98 is a suture 220). In such examples, the tubular sheath 12 may be configured to expose a portion of its lumen 90 immediately before or substantially coincident with the insertion of a portion of the expandable balloon 14 that is housed by the respective portion of the tubular sheath 12.

A clinician may then remove the tubular sheath 12 from the catheter 16 (404). A clinician may remove the tubular sheath 12 from the catheter 16 in response to inserting the expandable balloon 14 into the introducer sheath 22. In some examples, a clinician may only remove the tubular sheath 12 from the catheter 16 once the expandable balloon is fully within the vasculature 24 of the patient 26. A clinician may remove the tubular sheath 12 by converting the tubular sheath 12 into an open configuration by disengaging the retaining member 98.

Figure 13:
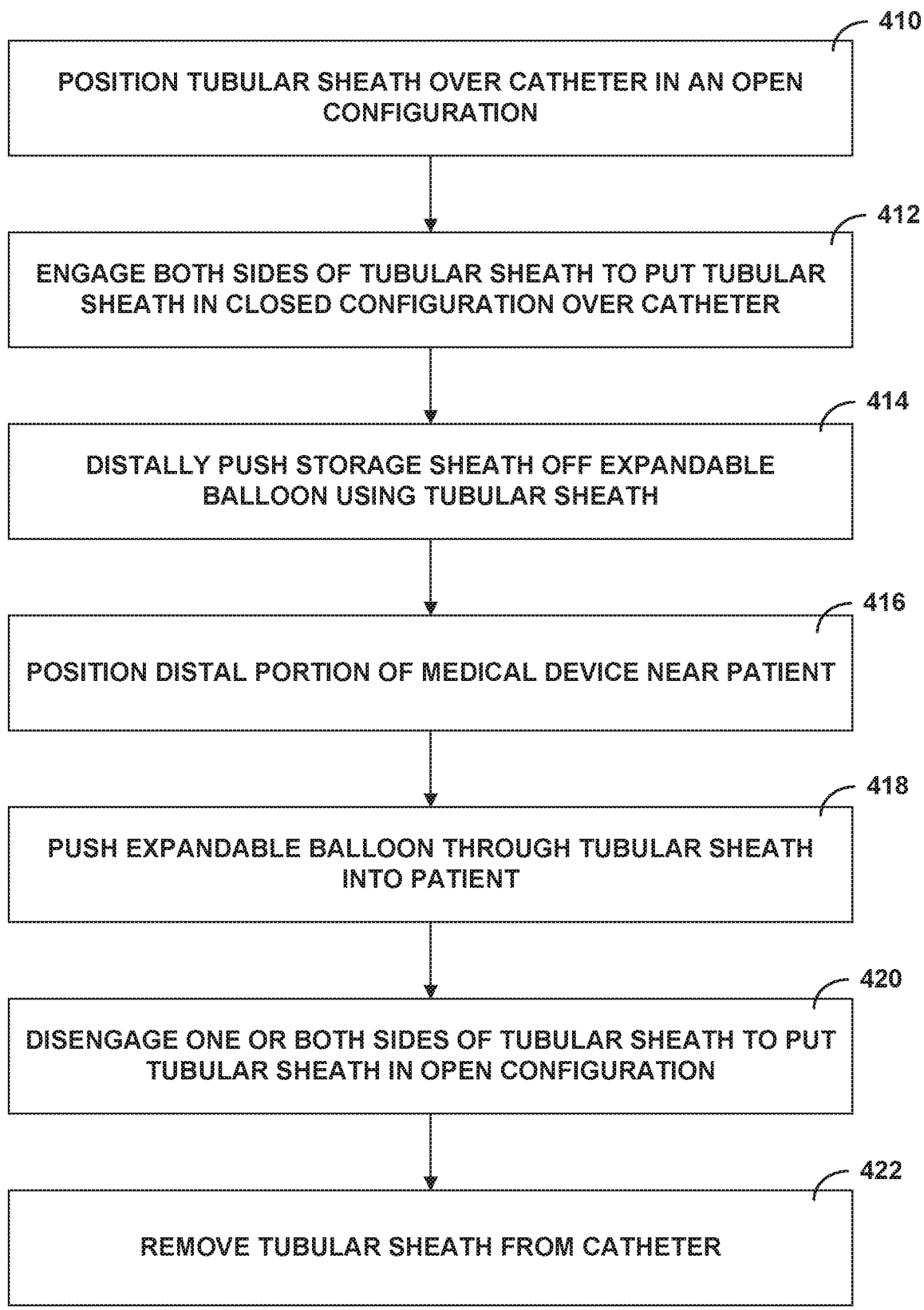
FIG. 13 is a flow diagram illustrating an example method of replacing a storage sheath housing an expandable balloon with a tubular sheath and inserting the expandable balloon into a patient.

FIG. 13 is a flow diagram illustrating a method of inserting an expandable balloon 14 using a tubular sheath 312. As discussed herein, in addition to housing/enclosing the expandable balloon 14, tubular sheaths 312 may be configured to replace an initial sheath (e.g., a non-splittable sheath that a catheter 16 and expandable balloon 14 are shipped with). Although the technique of FIG. 13 will be described with reference to the medical device 10 and other components illustrated in FIGS. 11A-11C, it will be appreciated that the technique of FIG. 13 may be used with any of the medical devices described herein. The flow diagram of FIG. 13 is discussed in conjunction with FIGS. 14A-14G for purposes of clarity only.

Figure 14A:
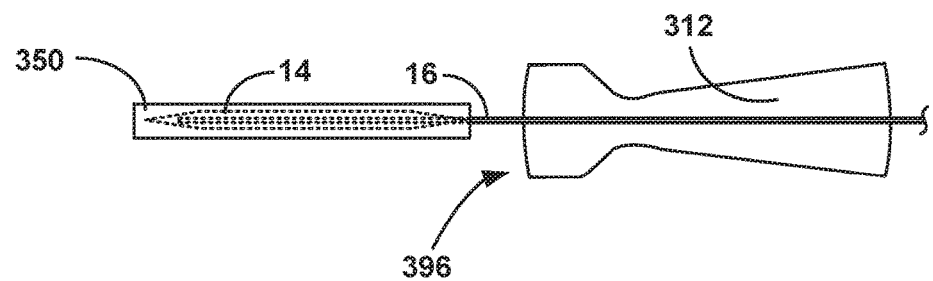
FIGS. 14A-14G are conceptual and schematic diagrams illustrating a use of a tubular sheath, including an example tubular sheath being located on an example catheter (FIG. 14A), being closed on the example catheter (FIG. 14B), distally pushing an example storage catheter (FIG. 14C), replacing the storage catheter (FIG. 14D), being located proximal to an example introducer sheath (FIG. 14E), being pushed proximally by the example introducer sheath (FIG. 14F), and being opened on the example catheter (FIG. 14G), respectively.
Figure 14B:
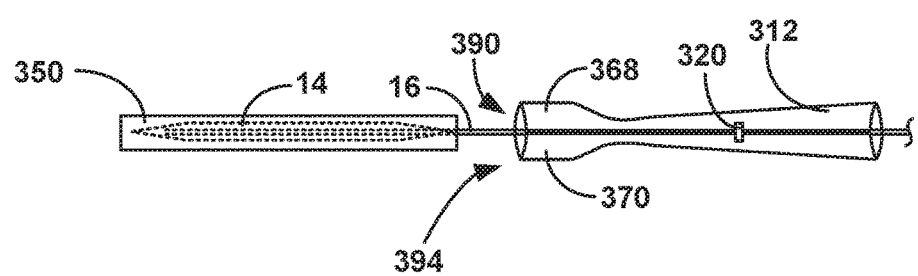

In FIG. 14A, a clinician may locate the tubular sheath 312 adjacent to a catheter 16 in an open configuration 396 (410). The clinician may orient the tubular sheath 312 at a location proximal to the expandable balloon 14 in the open configuration 396. An expandable balloon 14 may be arranged on the catheter 16. The expandable balloon 14 may be housed on the catheter 16 in a storage sheath 350. The storage sheath 350 may be configured to house the expandable balloon 14 from manufacture until such a time when the expandable balloon 14 is being prepped for clinical use. In FIG. 14B, a clinician may close the tubular sheath 312 (e.g., actuate the tubular sheath 312 to the closed configuration 394) around the catheter 16 such that the catheter 16 is within the inner lumen 390 of the tubular sheath 312 (412). In order to retain the tubular sheath 312 in the closed configuration 394, a clinician will engage the retaining member 98, for example the clasp 320, across the two sides 368, 370 of the tubular sheath 312.

Figure 14C:
Figure 14D:
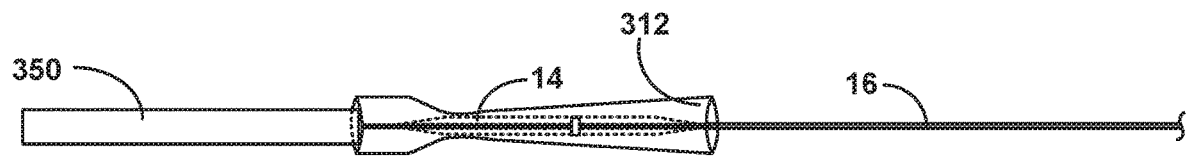

In FIG. 14C, a clinician may distally move the tubular sheath 312 relative to the catheter 16 until the tubular sheath 312 engages with and distally moves the storage sheath 350 (414). In some examples the tubular sheath 312 may have specific pushing features that engage with and distally push the storage sheath 350. In other examples, the wall of the distal end 366 of the tubular sheath 312 may distally push the storage sheath 350. The expandable balloon 14 stays in place relative to the catheter 16 as the clinician distally moves the storage sheath 350 over the expandable balloon 14. The clinician may distally push the tubular sheath 312 until the storage sheath 350 is entirely off of the catheter 16 as depicted in FIG. 14D. The tubular sheath 312 may be configured to not contact, or at least minimally contact, the expandable balloon 14 while distally pushing the storage sheath 350. Once the storage sheath 350 is entirely off of the catheter 16, the clinician may discard the storage sheath 350. In response to the tubular sheath 312 replacing the storage sheath 350 on the catheter 16, the clinician may position the distal portion 18 of the catheter 16 near an introducer sheath 22 that is inserted in a patient 26 (416).

Figure 14E:
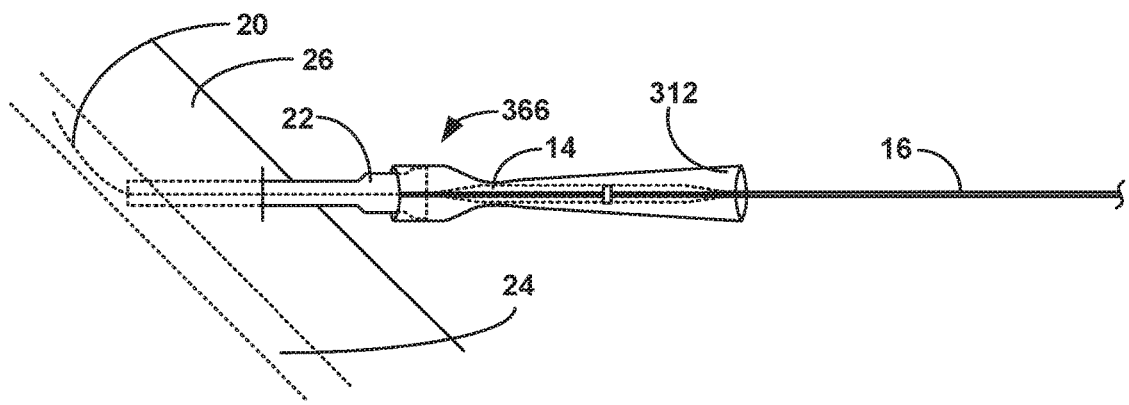

In FIG. 14E, the distal end 366 of the tubular sheath 312 receives the introducer sheath 22 that is inserted in a patient 26. The introducer sheath 22 may terminate in vasculature 24 of the patient 26. The clinician may distally move the catheter 16 and expandable balloon 14 with the tubular sheath 312 as the tubular sheath 312 receives the introducer sheath 22 (or is received by the introducer sheath 22 or otherwise mates with a proximal end of the introducer sheath 22). The clinician may guide the catheter 16 onto the introducer sheath 22 using a guidewire 20 that extends proximally from the introducer sheath 22. The clinician may insert the guidewire 20 into the guidewire lumen 42 of the catheter 16. In some examples, the distal end 366 of the tubular sheath 312 may act as a Luer connector that engages a Luer connection of the introducer sheath 22 (e.g., the clinician may thread internal threads 322 of the tubular sheath 312 onto threads 23 of the introducer sheath 22 as the introducer sheath 22 is received by the tubular sheath 312).

Figure 14F:
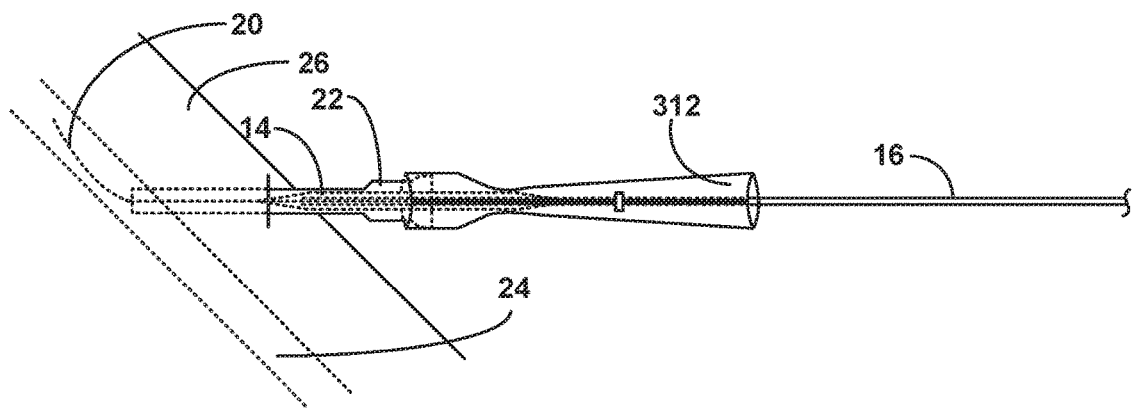
Figure 14G:
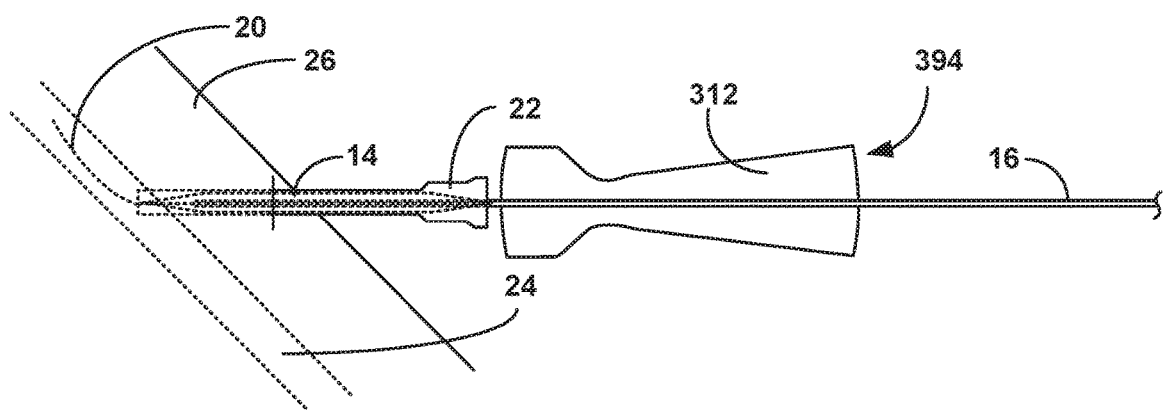

Once the tubular sheath 312 is stably received by the introducer sheath 22 (e.g., using a Luer connection), the clinician may push the expandable balloon 14 and catheter 16 into the introducer sheath 22/patient 26 (416). The clinician pushing the expandable balloon 14 into the introducer sheath 22 may include the clinician advancing the expandable balloon 14 and catheter 16 over the guidewire 20 into the introducer sheath 22 while the tubular sheath 312 remains stationary (e.g., stationary relative to the introducer sheath 22) as depicted in FIG. 14F. The clinician may push the expandable balloon 14 into the introducer sheath 22 by distally pushing the catheter 16 and/or catheter 16 hub 38. In this way, the clinician may insert the expandable balloon 14 into the introducer sheath 22 and therein introduce the expandable balloon 14 into the vasculature 24 of a patient 26 without manually handling or otherwise contacting an external surface 48 of the expandable balloon 14 in a notable manner.

Once the expandable balloon 14 is entirely within the introducer sheath 22/patient 26/vasculature 24, the clinician may disengage the retaining member 98, such as by unclasping the clasp 320, of the tubular sheath 312 to enable the tubular sheath 312 to be opened (e.g., actuated into the open configuration 396) to expose the inner lumen 390 of the tubular sheath 312 (420). In some examples, the clinician may proximally slide the tubular sheath 312 away from the patient before the retaining member 98 disengages one or both sides 68, 70 of the tubular sheath 312. Where a distal end 366 of the tubular sheath 312 includes a Luer fitting to mate with the introducer sheath 22, the clinician may disengage the tubular sheath 312 from the introducer sheath 22 (e.g., by rotating the tubular sheath 312 relative to the introducer sheath 22 where the Luer fitting includes threads) before proximally sliding the tubular sheath 312 away from the patient. Configuring the tubular sheath 312 such that a clinician may proximally slide the tubular sheath 312 on the catheter 16 after housing the expandable balloon 14 through the act of insertion and prior to removing the tubular sheath 312 may reduce the complexity of the insertion process of the expandable balloon 14. Upon exposing the inner lumen 390 of the tubular sheath 312, the clinician removes the tubular sheath 312 from the catheter 16 (422). The clinician may remove the tubular sheath 312 from the catheter 16 in a radially outward or transverse direction.

In other embodiments, the clinician may remove the storage sheath 350 by sliding the storage sheath 350 distally while holding the catheter 16. The clinician may then lay the expandable balloon 14 on the tubular sheath 312 without touching the expandable balloon, and then moving the tubular sheath 312 to the closed position and engaging the retaining member 98 to retain the tubular sheath 312 in the closed position. This method may enable the expandable balloon 14 to be stored in a slight relaxed position during shipping and storage, but be more tightly compressed by the tubular sheath 312. Further still, this method enables the tubular sheath 312 to be placed around the expandable balloon 14 without sliding over the expandable balloon 14, which sliding could potentially damage the expandable balloon 14 or any coating thereon.

Various examples of the disclosure have been described. These and other examples are within the scope of the following claims.

What is claimed is:

1. A medical device comprising:
   a tubular sheath having an outer wall and an inner wall that defines an inner lumen configured to house an expandable balloon that is attached to a distal portion of a catheter, wherein the tubular sheath includes a longitudinal slit through the tubular sheath, wherein the longitudinal slit extends substantially parallel to a longitudinal axis of the tubular sheath and defines a first side and a second side of the longitudinal slit, wherein the first side is joined with the second side, wherein the longitudinal slit exposes the inner lumen from a proximal end of the tubular sheath to a distal end of the tubular sheath; and
   a retaining member that is configured to engage the tubular sheath on both sides of the longitudinal slit to retain the tubular sheath in a closed configuration around the expandable balloon.

2. The medical device of claim 1, wherein the retaining member is configured to disengage one or both sides of the longitudinal slit to thereby convert the tubular sheath into an open configuration such that the inner lumen is exposed and the tubular sheath can be removed from around the expandable balloon or the catheter.

3. The medical device of claim 1, wherein the retaining member comprises a protective sleeve that substantially covers an outer surface of the tubular sheath.

4. The medical device of claim 3, wherein the protective sleeve comprises a plurality of longitudinal perforations extending through a wall of the protective sleeve in a direction substantially parallel to the longitudinal axis of the tubular sheath.

5. The medical device of claim 3, wherein the protective sleeve is configured to be peelable along the longitudinal axis of the tubular sheath.

6. The medical device of claim 3, wherein the protective sleeve comprises a film that has been heat shrunk onto the outer surface of the tubular sheath.

7. The medical device of claim 3, wherein the protective sleeve includes a tab attached to an end of the protective sleeve, wherein the protective sleeve is configured to be removed from the tubular sheath in a controlled manner in response to a force above a threshold force being exerted upon the tab.

8. The medical device of claim 1, wherein the retaining member comprises a notched groove that extends longitudinally along the longitudinal axis of the tubular sheath, wherein the notched groove aligns with the longitudinal slit of the tubular sheath.

9. The medical device of claim 1, wherein the retaining member comprises a strip of adhesive that substantially covers the longitudinal slit to adhere the sides of the tubular sheath on each side of the longitudinal slit to each other, wherein the strip of adhesive is configured to be removeable along the longitudinal axis of the tubular sheath.

10. The medical device of claim 1, wherein the retaining member comprises a suture that is configured to stitch together the tubular sheath across the longitudinal slit.

11. The medical device of claim 10, wherein the suture includes a tab attached to an end of the suture, wherein the suture is configured to unravel in a controlled manner in response to a force above a threshold force being exerted upon the tab.

12. The medical device of claim 1, wherein the retaining member comprises at least one ring that is configured to extend around a circumference of the tubular sheath, wherein the at least one ring is slideable along the longitudinal axis of the tubular sheath to remove the at least one ring from the tubular sheath.

13. The medical device of claim 1, wherein the retaining member comprises a clasp on the tubular sheath on one side of the longitudinal slit and a mating element on the tubular sheath on the other side of the longitudinal slit, wherein the clasp is configured to engage the mating element to retain the tubular sheath in the closed configuration.

14. The medical device of claim 1, wherein the tubular sheath is configured to be slideable over the catheter, wherein the tubular sheath is configured to engage and distally displace a storage sheath that is covering the expandable balloon when the expandable balloon is on the distal portion of the catheter without substantial contact to the expandable balloon when the tubular sheath is on the catheter proximal to the protective sleeve.

15. The medical device of claim 1, wherein a distal portion of the tubular sheath is flared outward from the longitudinal axis of the tubular sheath.

16. The medical device of claim 1, wherein a proximal portion of the tubular sheath is flared outward from the longitudinal axis of the tubular sheath.

17. The medical device of claim 1, wherein the inner wall that defines the inner lumen of the tubular sheath is coated with a lubricious material to reduce friction between the tubular sheath and the expendable balloon.

18. The medical device of claim 1, further comprising a Luer fitting on a distal end of the tubular sheath, wherein the Luer fitting comprises a structural weakness aligned with the longitudinal slit to enable the Luer fitting to be controllably split along the structural weakness.

19. The medical device of claim 1, wherein the expandable balloon is coated with a drug coating.

20. The medical device of claim 1, wherein a thickness between the inner and outer walls of the tubular sheath is substantially constant throughout the tubular sheath.

21. The medical device of claim 1, wherein the tubular sheath comprises at least one of poly(tetrafluoroethylene), high density polyethylene, and low density polyethylene.

22. The medical device of claim 1, wherein the balloon is in a deflated state on the distal portion of the catheter, and a diameter of the inner lumen is configured to be greater than an outer diameter of the expandable balloon in the deflated state.

23. The medical device of claim 22, wherein a length of the tubular sheath along the longitudinal axis of the tubular sheath is configured to be greater than a length of the expandable balloon along a longitudinal axis of the expandable balloon in the deflated state.

24. A method of inserting expandable balloons, the method comprising:
 positioning a distal portion of a catheter of a medical device immediately proximal to an introducer sheath implanted in a body of a patient, the medical device comprising:
  a tubular sheath having an outer wall and an inner wall that defines an inner lumen configured to house an expandable balloon that is attached to the distal portion of the catheter, wherein the tubular sheath includes a longitudinal slit through the tubular sheath, wherein the longitudinal slit extends substantially parallel to a longitudinal axis of the tubular sheath and defines a first side and a second side of the longitudinal slit, wherein the first side is joined with the second side, wherein the longitudinal slit exposes the inner lumen from a proximal end of the tubular sheath to a distal end of the tubular sheath, and
  a retaining member that is configured to engage the tubular sheath on both sides of the longitudinal slit to retain the tubular sheath in a closed configuration around the expandable balloon,
 disengaging the retaining member from the tubular sheath to thereby convert the tubular sheath into an open configuration after inserting the expandable balloon into the introducer sheath; and
 removing the tubular sheath from the catheter in response to converting the tubular sheath into the open configuration.

25. A method of inserting expandable balloons, the method comprising:
 positioning an inner lumen defined by an inner wall of a tubular sheath over a catheter that is configured to navigate vasculature of a patient, an expandable balloon attached to a distal portion of the catheter and a storage sheath covering the expandable balloon on the distal portion of the catheter, wherein the tubular sheath is positioned proximal to the storage sheath, the tubular sheath comprising:
  an outer wall and the inner wall,
  a longitudinal slit through the tubular sheath, wherein the longitudinal slit extends substantially parallel to a longitudinal axis of the tubular sheath and defines a first side and a second side of the longitudinal slit, wherein the longitudinal slit exposes the inner lumen, and
  a retaining member that is configured to engage the tubular sheath on both sides of the longitudinal slit to retain the tubular sheath in a closed configuration around the expandable balloon,
 engaging the retaining member across both sides of the longitudinal slit to retain the tubular sheath in a closed configuration with the catheter within the inner lumen of the tubular sheath;
 distally pushing the tubular sheath until the tubular sheath engages and distally pushes the storage sheath off the catheter without substantial contact to the expandable balloon;
 locating the distal portion of the catheter immediately proximal to an introducer sheath implanted in the body of a patient;
 pushing the expandable balloon through the tubular sheath into the introducer sheath;
 disengaging the retaining member from at least side of the tubular sheath across the longitudinal slit to thereby convert the tubular sheath into an open configuration in response to inserting the expandable balloon into the introducer sheath; and
 removing the tubular sheath from the catheter in response to converting the tubular sheath into the open configuration.

26. A medical device comprising:
 a catheter that is configured to navigate vasculature of a body of a patient;
 an expandable balloon arranged in a deflated state on a distal portion of the catheter;
 a tubular sheath having an outer wall and an inner wall that defines an inner lumen that is configured to house the expandable balloon in the deflated state on the distal portion of the catheter, a diameter of the inner lumen configured to be greater than an outer diameter of the expandable balloon in the deflated state, a length of the tubular sheath along a longitudinal axis of the tubular sheath configured to be greater than a length of the expandable balloon along a longitudinal axis of the expandable balloon in the deflated state, wherein the tubular sheath includes a longitudinal slit through the tubular sheath, wherein the longitudinal slit extends substantially parallel to a longitudinal axis of the tubular sheath and defines a first side and a second side of the longitudinal slit, wherein the longitudinal slit exposes the inner lumen from a proximal end of the tubular sheath to a distal end of the tubular sheath; and
 a retaining member that is configured to engage the tubular sheath on both sides of the longitudinal slit to retain the tubular sheath in a closed configuration around the expandable balloon.

* * * * *